(12) United States Patent
Yang et al.

(10) Patent No.: US 7,026,494 B1
(45) Date of Patent: Apr. 11, 2006

(54) POLYMERIZATION CATALYSTS FOR PRODUCING HIGH MELT INDEX POLYMERS WITHOUT THE USE OF HYDROGEN

(75) Inventors: Qing Yang, Bartlesville, OK (US); Michael D. Jensen, Bartlesville, OK (US); Matthew G. Thorn, Bartlesville, OK (US); Max P. McDaniel, Bartlesville, OK (US); Joel L. Martin, Bartlesville, OK (US); Tony R. Crain, Niotaze, KS (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 11/032,557

(22) Filed: Jan. 10, 2005

(51) Int. Cl.
*C07F 17/00* (2006.01)
*B01J 31/00* (2006.01)
*G08F 4/64* (2006.01)

(52) U.S. Cl. .......................... 556/11; 556/12; 502/120; 502/158; 526/128; 526/160; 526/943

(58) Field of Classification Search .................. 556/11, 556/12; 502/120, 158; 526/126, 160, 943
See application file for complete search history.

(56) References Cited

U.S. PATENT DOCUMENTS

| | | |
|---|---|---|
| 4,931,417 A | 6/1990 | Miya et al. |
| 4,939,217 A | 7/1990 | Stricklen |
| 5,886,202 A | 3/1999 | Jung et al. |
| 5,907,021 A | 5/1999 | Turner et al. |
| 5,968,863 A | 10/1999 | Nifant'ev et al. |
| 6,051,728 A | 4/2000 | Resconi et al. |
| 6,114,480 A | 9/2000 | Shamshoum et al. |
| 6,143,911 A | 11/2000 | Fujita et al. |
| 6,376,418 B1 | 4/2002 | Shamshoum et al. |
| 2002/0169260 A1 | 11/2002 | Resconi et al. |
| 2003/0120015 A1* | 6/2003 | Resconi et al. ............. 526/351 |
| 2003/0158356 A1* | 8/2003 | Resconi et al. ............. 526/127 |

FOREIGN PATENT DOCUMENTS

| | | |
|---|---|---|
| EP | 0 435 250 | 7/1991 |
| EP | 0 435 251 | 7/1991 |
| EP | 0 802 206 | 10/1997 |
| EP | 1 302 486 A1 * | 4/2003 |
| EP | 1 416 000 | 5/2004 |
| WO | WO 01/44319 A2 * | 6/2001 |
| WO | WO 01/90205 A1 * | 11/2001 |

OTHER PUBLICATIONS

Giannetti et al., "Homogeneous Ziegler-Natta Catalysis. II. Ethylene Polymerization by IVB Transition Metal Complexes . . . ", J. Polymer Sci. vol. 23, pp. 2117-2134 (1985).
Horton et al., "A Structurally Distorted Ligand In An Electron-Deficient Dizirconocene Cation: . . . ", Angew. Chem. Int. Ed., vol. 31, No. 7, pp. 876-878 (England 1992).
Kaminsky et al., "Standardization Polymerizations Of Ethylene And Propene WIth Bridged And Unbridged Metallocene Derivatives . . . ", Makromol. Chem. vol. 193, pp. 1643-1651 (1992).
Fierro et al., "Asymmetric Zirconocene Precursors For Catalysis Of Propylene Polymerization", J. Polymer Sci., vol. 32, pp. 2817-2824 (1994).
Luinstra, G.A., "Synthesis And Reactivity Of Titanocene And Zirconocene Triflates", J. Organometallic Chemistry, vol. 517, pp. 209-215 (1996).
Sztáray et al., "Geometry And Electronic Structure Of bis(tetrahydridoborato) bis(cyclopentadienyl)zirconium(IV)", J. Organometallic Chemistry, vol. 582, pp. 267-272 (1999).
Lunistra et al., "Synthesis And Reactivity of Cp2ZrH(OSO2CF3), A Soluble Alternative For Schwartz's Reagent . . . ", Organometallics, vol. 14, pp. 1551-1552 (1995).
Fandos et al., "Synthesis And Characterisation Of Group 4 Metallocene Alkoxide Complexes . . . ", J. Organometallic Chemistry, vol. 606, pp. 156-162 (2000).
Alt et al., "Effect Of The Nature Of Metallocene Complexes Of Group IV Metals On Their Performance In Catalytic Ethylene . . . ", Chem. Rev., vol. 100, pp. 1205-1221 (2000).

* cited by examiner

*Primary Examiner*—Porfirio Nazario-Gonzalez
(74) *Attorney, Agent, or Firm*—Womble Carlye Sandridge & Rice, PLLC

(57) ABSTRACT

Various catalyst compositions including the contact product of at least one ansa-metallocene compound, at least one organoaluminum compound, and at least one activator-support are disclosed. Processes for forming such compositions and for forming polyolefins with such compositions are also disclosed. Metallocene compounds are also presented.

29 Claims, No Drawings

POLYMERIZATION CATALYSTS FOR PRODUCING HIGH MELT INDEX POLYMERS WITHOUT THE USE OF HYDROGEN

FIELD OF THE INVENTION

This invention relates to the field of organometal compositions, olefin polymerization catalyst compositions, methods for the polymerization and copolymerization of olefins using a catalyst composition, and polyolefins.

BACKGROUND OF THE INVENTION

Low molecular weight, or high melt index (MI), polyethylene (both homopolymer and copolymer) is widely used in bimodal resins, extrusion coating resins, and rotational and injection molding resins. In conventional polymerization processes, high MI polyethylene is produced by introducing hydrogen during the polymerization process. Unfortunately, the large quantity of hydrogen needed to produce high MI polymer suppresses the activity of the catalyst.

A few metallocene catalyst systems are reported that produce high MI polyethylene without the need for hydrogen. For example, some catalyst systems employing carbon-bridged cyclopentadienyl indenyl metallocenes have been shown to produce relatively lower molecular weight polyethylene when activated with methylaluminoxanes (MAO), but the activity of such catalyst systems is typically poor (*Makromol. Chem.* 1992, 193, 1643 and *J Polym. Sci. Part A*, 1994, 32, 2817).

Thus, there remains a need for a metallocene catalyst composition having a high activity, and a process for forming such a composition, that can be used to produce low molecular weight, high melt index polyethylene without the use of hydrogen.

SUMMARY OF THE INVENTION

The present invention is directed generally to new catalyst compositions, methods for preparing catalyst compositions, methods for using the catalyst compositions to polymerize olefins, and metallocene compounds that may be used in such compositions and processes.

In accordance with the present invention, a catalyst composition comprises the contact product of an ansa-metallocene compound, an organoaluminum compound, and an activator-support. The ansa-metallocene compound has the structure:

(i)

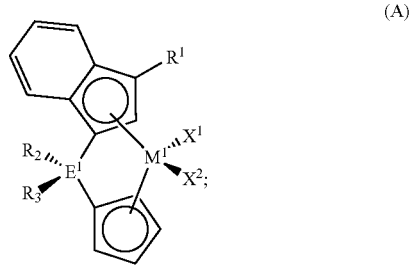

(A)

wherein $M^1$ is titanium or zirconium; $X^1$ and $X^2$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms; $R^1$ is an alkyl group having from 1 to about 20 carbon atoms, an alkyl silyl group, an alkenyl group, an alkynyl group, or a silyl group; $E^1$ is carbon or silicon; and $R^2$ and $R^3$ independently are an alkyl group having from 1 to about 20 carbon atoms, an alkyl silyl group having from 1 to about 20 carbon atoms, an aryl group, an alkenyl group having from 2 to about 20 carbon atoms, an alkynyl group having from 2 to about 20 carbon atoms, a silyl group, or a hydride group; or (ii)

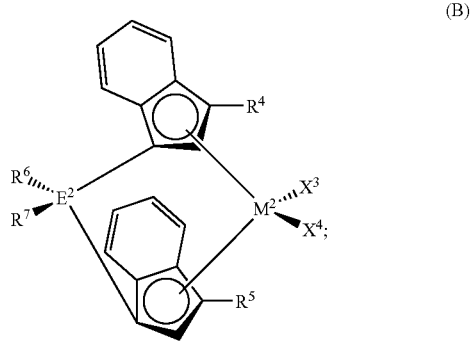

(B)

wherein $M^2$ is titanium or zirconium; $X^3$ and $X^4$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms; $R^4$ and $R^5$ independently are an alkyl group having from 1 to about 20 carbon atoms, an alkyl silyl group having from 1 to about 20 carbon atoms, an alkenyl group having from 2 to about 20 carbon atoms, or an alkynyl group having from 2 to about 20 carbon atoms; $E^2$ is carbon or silicon; and $R^6$ and $R^7$ independently are an aryl group, an alkyl group having from 1 to about 20 carbon atoms, an alkenyl group having from 2 to about 20 carbon atoms, or an alkynyl group having from 2 to about 20 carbon atoms.

According to various aspects of the present invention, $R^1$ may be a propyl group, a 1-butenyl group, or a trimethyl silyl group, and $R^2$ and $R^3$ each may be a methyl group. According to various other aspects of the present invention, $R^4$ and $R^5$ each may be a propyl group or an iso-butyl group, and $R^6$ and $R^7$ each may be a phenyl group or a methyl group.

Organoaluminum compounds that may be employed in this and other aspects of the present invention include compounds having the formula:

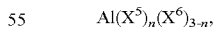

wherein $(X^5)$ is a hydrocarbyl having from 1 to about 20 carbon atoms, $(X^6)$ is an alkoxide or an aryloxide having from 1 to about 20 carbon atoms, halide, or hydride, and n is a number from 1 to 3, inclusive. For example, the organoaluminum compound may be trimethylaluminum, triethylaluminum, tri-n-propylaluminum, diethylaluminum ethoxide, tri-n-butylaluminum, diisobutylaluminum hydride, triisobutylaluminum, diethylaluminum chloride, or any combination thereof.

The activator-support may comprise a chemically-treated solid oxide, for example, fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, or any combination thereof.

According to another aspect of the present invention, a process for producing a catalyst composition comprises contacting an ansa-metallocene compound, a chemically-treated solid oxide, and an organoaluminum compound. The ansa-metallocene compound has the structure:

(i)

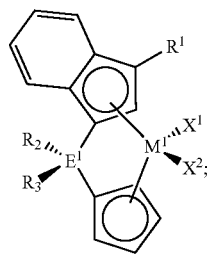

wherein $M^1$ is titanium or zirconium; $X^1$ and $X^2$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms; $R^1$ is an alkyl group having from 1 to about 20 carbon atoms, an alkyl silyl group, an alkenyl group, an alkynyl group, or a silyl group; $E^1$ is carbon or silicon; and $R^2$ and $R^3$ independently are an alkyl group having from 1 to about 20 carbon atoms, an alkyl silyl group having from 1 to about 20 carbon atoms, an aryl group, an alkenyl group having from 2 to about 20 carbon atoms, an alkynyl group having from 2 to about 20 carbon atoms, a silyl group, or a hydride group; or (ii)

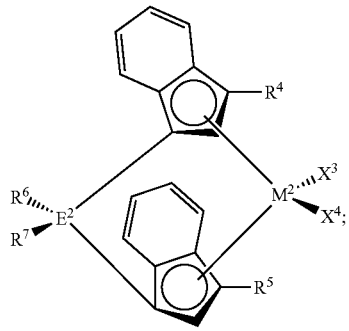

(B)

wherein $M^2$ is titanium or zirconium; $X^3$ and $X^4$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms; $R^4$ and $R^5$ independently are an alkyl group having from 1 to about 20 carbon atoms, an alkyl silyl group having from 1 to about 20 carbon atoms, an alkenyl group having from 2 to about 20 carbon atoms, or an alkynyl group having from 2 to about 20 carbon atoms; $E^2$ is carbon or silicon; and $R^6$ and $R^7$ independently are an aryl group, an alkyl group having from 1 to about 20 carbon atoms, an alkenyl group having from 2 to about 20 carbon atoms, or an alkynyl group having from 2 to about 20 carbon atoms.

According to yet another aspect of the present invention, a process for forming a polymer having a high melt index in the absence of hydrogen is provided. The process comprises contacting a catalyst composition with at least one type of olefin monomer under polymerization conditions, the catalyst composition comprising an ansa-metallocene compound, a chemically-treated solid oxide, and an organoaluminum compound. The ansa-metallocene compound has the structure:

(i)

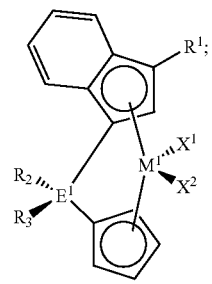

(A)

wherein $M^1$ is titanium or zirconium; $X^1$ and $X^2$ independently are a halogen, alkyl group, alkyl silyl group, aryl group, alkenyl group, alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms; $R^1$ is an alkyl group having from 1 to about 20 carbon atoms, an alkyl silyl group, an alkenyl group, an alkynyl group, or a silyl group; $E^1$ is carbon or silicon; and $R^2$ and $R^3$ independently are an alkyl group having from 1 to about 20 carbon atoms, an alkyl silyl group having from 1 to about 20 carbon atoms, an aryl group, an alkenyl group having from 2 to about 20 carbon atoms, an alkynyl group having from 2 to about 20 carbon atoms, a silyl group, or a hydride group; or (ii)

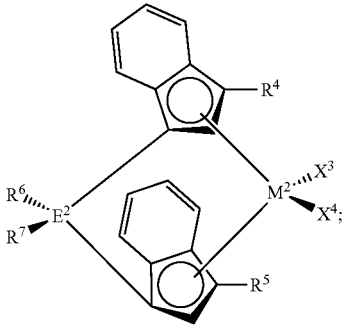

(B)

wherein $M^2$ is titanium or zirconium; $X^3$ and $X^4$ independently are a halogen, alkyl group, alkyl silyl group, aryl group, alkenyl group, alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms; $R^4$ and $R^5$ independently are an alkyl group having from 1 to about 20 carbon atoms, an alkyl silyl group having from 1 to about 20 carbon atoms, an alkenyl group having from 2 to about 20 carbon atoms, or an alkynyl group having from 2 to about 20 carbon atoms; $E^2$ is carbon or silicon; and $R^6$ and $R^7$ independently are an aryl group, an alkyl group having from 1 to about 20 carbon atoms, an alkenyl group having from 2 to about 20 carbon atoms, or an alkynyl group having from 2 to about 20 carbon atoms.

Metallocene compounds are also provided. The metallocene compounds are represented by the structures:

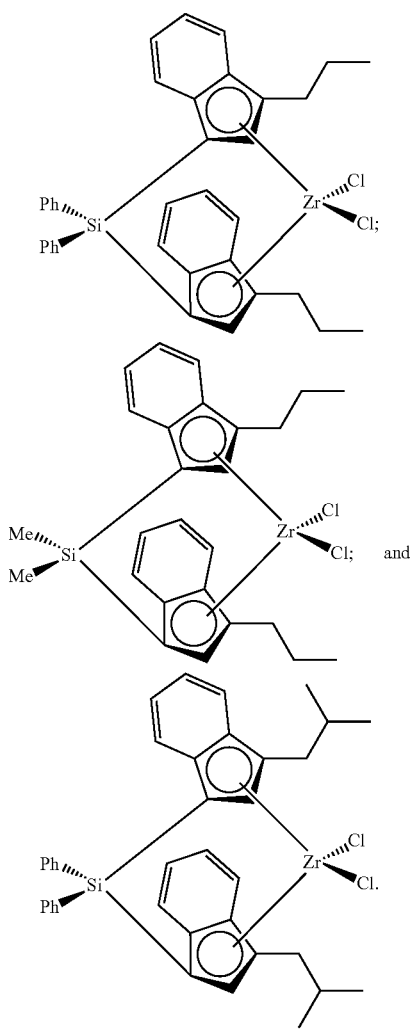

DEFINITIONS

To define more clearly the terms used herein, the following definitions are provided. To the extent that any definition or usage provided by any document incorporated herein by reference conflicts with the definition or usage provided herein, the definition or usage provided herein controls.

The term "polymer" is used herein to mean homopolymers comprising ethylene and copolymers of ethylene and another olefinic comonomer. "Polymer" is also used herein to mean homopolymers and copolymers of any other polymerizable monomer disclosed herein.

The term "cocatalyst" is used generally herein to refer to the organoaluminum compounds that may constitute one component of the catalyst composition. Additionally, "cocatalyst" refers to the optional components of the catalyst composition including, but not limited to, aluminoxanes, organoboron compounds, organozinc compounds, or ionizing ionic compounds, as disclosed herein. The term "cocatalyst" may be used regardless of the actual function of the compound or any chemical mechanism by which the compound may operate. In one aspect of this invention, the term "cocatalyst" is used to distinguish that component of the catalyst composition from the metallocene compound.

The term "fluoroorgano boron compound" is used herein with its ordinary meaning to refer to neutral compounds of the form $BY_3$. The term "fluoroorgano borate compound" also has its usual meaning to refer to the monoanionic salts of a fluoroorgano boron compound of the form [cation]$^+$ [$BY_4$]$^-$, where Y represents a fluorinated organic group. For convenience, fluoroorgano boron and fluoroorgano borate compounds are typically referred to collectively by "organoboron compounds" or by either name as the context requires.

The term "precontacted" mixture is used herein to describe a first mixture of catalyst components that are contacted for a first period of time prior to the first mixture being used to form a "postcontacted" or second mixture of catalyst components that are contacted for a second period of time. Typically, the precontacted mixture describes a mixture of metallocene compound (or compounds), olefin monomer, and organoaluminum compound (or compounds), before this mixture is contacted with the activator-support and optional additional organoaluminum compound. Thus, precontacted describes components that are used to contact each other, but prior to contacting the components in the second, postcontacted mixture. Accordingly, this invention may occasionally distinguish between a component used to prepare the precontacted mixture and that component after the mixture has been prepared. For example, according to this description, it is possible for the precontacted organoaluminum compound, once it is contacted with the metallocene and the olefin monomer, to have reacted to form at least one different chemical compound, formulation, or structure from the distinct organoaluminum compound used to prepare the precontacted mixture. In this case, the precontacted organoaluminum compound or component is described as comprising an organoaluminum compound that was used to prepare the precontacted mixture.

Similarly, the term "postcontacted" mixture is used herein to describe a second mixture of catalyst components that are contacted for a second period of time, and one constituent of which is the "precontacted" or first mixture of catalyst components that were contacted for a first period of time. Typically, the term "postcontacted" mixture is used herein to describe the mixture of the metallocene compound, olefin monomer, organoaluminum compound, and chemically-treated solid oxide, formed from contacting the precontacted mixture of a portion of these components with any additional components added to make up the postcontacted mixture. Generally, the additional component added to make up the postcontacted mixture is the chemically-treated solid oxide and, optionally, may include an organoaluminum compound the same or different from the organoaluminum compound used to prepare the precontacted mixture, as described herein. Accordingly, this invention also may occasionally distinguish between a component used to prepare the postcontacted mixture and that component after the mixture has been prepared.

The term "metallocene", as used herein, describes a compound comprising two $\eta^5$-cycloalkadienyl-type ligands in the molecule. Thus, the metallocenes of this invention are bis($\eta^5$-cyclopentadienyl-type ligand) compounds, wherein the $\eta^5$-cycloalkadienyl portions include cyclopentadienyl ligands, indenyl ligands, fluorenyl ligands, and the like, including partially saturated or substituted derivatives or analogs of any of these. Possible substituents on these ligands include hydrogen, therefore the description "substituted derivatives thereof" in this invention comprises partially saturated ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like. In some contexts, the metallocene is referred to simply as the "catalyst", in much the same way the term "cocatalyst" is used herein to refer to the organoaluminum compound. Unless otherwise specified, the following abbreviations are used: Cp for cyclopentadienyl; Ind for indenyl; and Flu for fluorenyl.

The terms "catalyst composition", "catalyst mixture", and the like do not depend upon the actual product resulting from the contact or reaction of the components of the mixtures, the nature of the active catalytic site, or the fate of the aluminum cocatalyst, the metallocene compound, any olefin monomer used to prepare a precontacted mixture, or the chemically-treated solid oxide after combining these components. Therefore, the terms "catalyst composition", "catalyst mixture", and the like may include both heterogeneous compositions and homogenous compositions.

The term "hydrocarbyl" is used herein to specify a hydrocarbon radical group that includes, but is not limited to aryl, alkyl, cycloalkyl, alkenyl, cycloalkenyl, cycloalkadienyl, alkynyl, aralkyl, aralkenyl, aralkynyl, and the like, and includes all substituted, unsubstituted, branched, linear, heteroatom substituted derivatives thereof.

The terms "chemically-treated solid oxide", "solid oxide activator-support", "acidic activator-support", "activator-support", "treated solid oxide compound", or simply "activator", and the like are used herein to indicate a solid, inorganic oxide of relatively high porosity, which exhibits Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide compound comprises the calcined contact product of at least one solid oxide compound with at least one electron-withdrawing anion source compound. Typically, the chemically-treated solid oxide comprises at least one ionizing, acidic solid oxide compound. The terms "support" and "activator-support" are not used to imply these components are inert, and such components should not be construed as an inert component of the catalyst composition.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

For any particular compound disclosed herein, unless otherwise specified, any general structure presented also encompasses all conformational isomers, regioisomers, and stereoisomers that may arise from a particular set of substituents. The general structure also encompasses all enantiomers, diastereomers, and other optical isomers whether in enantiomeric or racemic forms, as well as mixtures of stereoisomers, as the context requires.

DETAILED DESCRIPTION OF THE INVENTION

The present invention is directed generally to new catalyst compositions, methods for preparing catalyst compositions, methods for using the catalyst compositions to polymerize olefins, and metallocene compounds that may be used in such compositions and processes. The metallocenes can be characterized generally as bridged cyclopentadienyl 3-substituted indenyl metallocenes and meso, bridged 3-substituted bis-indenyl metallocenes. It has been discovered that the metallocenes of the present invention can be used to produce polyolefins having a high melt index, without the use of hydrogen. Notably, the compositions of the present invention achieve high activities.

In the absence of hydrogen, activated catalyst systems employing unbridged cyclopentadienyl 3-substituted indenyl metallocenes typically produce polyethylene having a melt index that is less than 10. Bridged cyclopentadienyl non-substituted indenyl metallocene is known to have a very poor activity in ethylene polymerization when activated with MAO (*Makromol. Chem.* 1992, 193, 1643 and *J Polym. Sci. Part A*, 1994, 32, 2817).

In contrast, under similar polymerization conditions, the catalyst systems of the present invention produce polyethylene having a high melt index, that is, a melt index of at least about 50. In one aspect, the systems of the present invention produce polyethylene having a melt index of from about 50 to about 300. In another aspect, the systems of the present invention produce polyethylene having a melt index of from about 300 to about 700. In still another aspect, the systems of the present invention produce polyethylene having a melt index of greater than about 700. Additionally, such metallocenes are highly active in ethylene polymerization when activated with solid acids according to the present invention.

Likewise, bridged bis-indenyl metallocenes, such as rac-Me$_2$SiInd$_2$ZrCl$_2$ and meso-Me$_2$Si(2-MeInd)$_2$ZrCl$_2$ typically produce fractional melt index polyethylene resins. However, as will be discussed in greater detail below, the bridged bis-indenyl metallocene compounds of the present invention result in a polymer having a high melt index.

According to one aspect of the present invention, a composition of matter is provided. The composition includes a metallocene compound, an activator-support, and an organoaluminum compound. Catalyst compositions including various combinations of these components including, but not limited to, at least one metallocene compound, at least one activator-support, at least one organoaluminum compound, and any combination of more than one metallocene compound, more than one activator-support, and more than one organoaluminum compound are also contemplated.

According to other aspects, the present invention is directed to a method of preparing a catalyst composition, a method of polymerizing olefins, and the like, in each case encompassing a metallocene compound, an activator-support, and at least one organoaluminum compound. The catalyst compositions optionally may be used with other catalyst systems to produce bimodal polymers. Notably, the catalyst systems of the present invention enable the olefin polymerization to proceed in the absence of costly aluminoxanes and organoborates. Nonetheless, such compounds optionally may be used if desired. New metallocene compounds are also provided by the present invention.

A. Catalyst Composition and Components

1. The Metallocene Compounds

The present invention is directed to various ansa-metallocenes that, when used in a catalyst composition, provide for the production of low molecular weight, high melt index polyolefins. According to one aspect of the present invention, the ansa-metallocene compound comprises a compound having the structure:

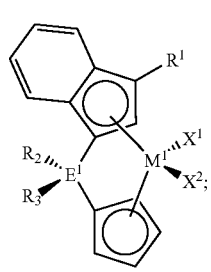

(A)

wherein $M^1$ is titanium or zirconium; $X^1$ and $X^2$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms; $R^1$ is an alkyl group having from 1 to about 20 carbon atoms, an alkyl silyl group, an alkenyl group, an alkynyl group, or a silyl group; $E^1$ is carbon or silicon; and $R^2$ and $R^3$ independently are an alkyl group having from 1 to about 20 carbon atoms, an alkyl silyl group having from 1 to about 20 carbon atoms, an aryl group, an alkenyl group having from 2 to about 20 carbon atoms, an alkynyl group having from 2 to about 20 carbon atoms, a silyl group, or a hydride group.

According to one aspect of the present invention, $R^1$ is a propyl group, a 1-butenyl group, or a trimethyl silyl group. According to another aspect of the present invention, $R^2$ and $R^3$ independently are a methyl group.

Thus, the present invention contemplates various metallocene compounds, including, but not limited to:

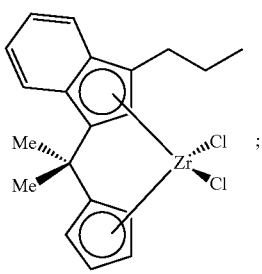

I-1

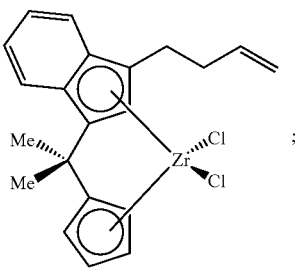

I-2

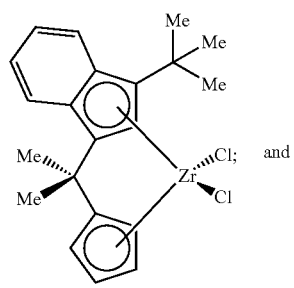

I-3 any combination thereof.

According to another aspect of the present invention, the meso ansa-metallocene comprises:

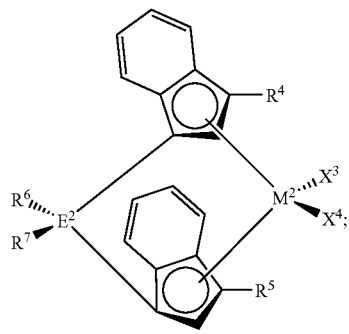

(B)

wherein $M^2$ is titanium or zirconium; $X^3$ and $X^4$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms; $R^4$ and $R^5$ independently are an alkyl group having from 1 to about 20 carbon atoms, an alkyl silyl group having from 1 to about 20 carbon atoms, an alkenyl group having from 2 to about 20 carbon atoms, or an alkynyl group having from 2 to about 20 carbon atoms, $E^2$ is carbon or silicon, and $R^6$ and $R^7$ independently are an aryl group or an alkyl group having from 1 to about 20 carbon atoms, an alkenyl group having from 2 to about 20 carbon atoms, or an alkynyl group having from 2 to about 20 carbon atoms.

According to one aspect of the present invention, $R^4$ and $R^5$ independently are a propyl group or an iso-butyl group. According to another aspect of the present invention, $R^6$ and $R^7$ independently are a phenyl group or a methyl group.

Thus, this aspect of the present invention encompasses numerous meso ansa-metallocenes, including, but not limited to:

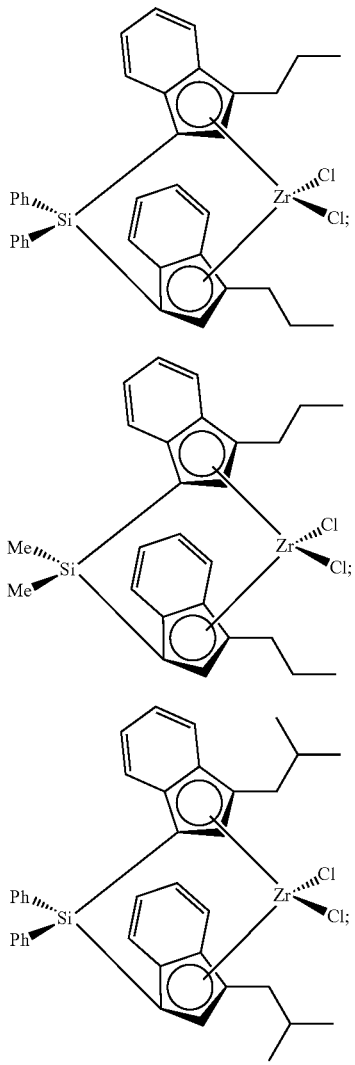

or any combination thereof. Additional examples of metallocene compounds that may be used with the present invention include, but are not limited to, those described in Giannetti, E., Nicoletti, G. M., Mazzocchi, R., *J Polm. Sci., Polym. Chem. Ed.*, 23, 2117–2133 (1985); Sztáray, B. Rosta, E., Böcskey, Z., Szepes, L., *J Organomet. Chem.*, 582, (1999) 267–272; Luinstra, G. A., Rief, U., Prosenc, M. H., *Organometallics* 1995, 14, 1551–1552; Luinstra, G. A., *J Organomet. Chem.*, 517, (1996) 209–215; Fandos, R., Hernandez, C., Otero, A., Rodriquez, A., Ruiz, M. J., Terreros, P., *J Organomet. Chem.*, 606, (2000) 156–162; Horton, A. D., Orgen, A. G., Angew., *Chem. Int. Ed. Engl.* 1992, 31(7), 876–878, U.S. Pat. No. 6,339,035; Balkwill, J. E., Cole, S. C., Coles, M. P., Hitchcock, P. B., *Inorg. Chem.*, 2002, 41, 3548–3552, each of which is incorporated by reference herein in its entirety.

2. The Chemically-Treated Solid Oxide

The present invention encompasses various catalyst compositions including an activator-support comprising a chemically-treated solid oxide.

The chemically-treated solid oxide exhibits enhanced acidity as compared to the corresponding untreated solid oxide compound. The chemically-treated solid oxide also functions as a catalyst activator as compared to the corresponding untreated solid oxide. While the chemically-treated solid oxide activates the metallocene in the absence of cocatalysts, it is not necessary to eliminate cocatalysts from the catalyst composition. The activation function of the activator-support is evident in the enhanced activity of catalyst composition as a whole, as compared to a catalyst composition containing the corresponding untreated solid oxide. However, it is believed that the chemically-treated solid oxide can function as an activator, even in the absence of an organoaluminum compound, aluminoxanes, organoboron compounds, or ionizing ionic compounds.

The chemically-treated solid oxide may comprise at least one solid oxide treated with at least one electron-withdrawing anion. While not intending to be bound by the following statement, it is believed that treatment of the solid oxide with an electron-withdrawing component augments or enhances the acidity of the oxide. Thus, the activator-support exhibits Lewis or Brønsted acidity that is typically greater than the Lewis or Brønsted acid strength than the untreated solid oxide, or the activator-support has a greater number of acid sites than the untreated solid oxide, or both. One method to quantify the acidity of the chemically-treated and untreated solid oxide materials is by comparing the polymerization activities of the treated and untreated oxides under acid catalyzed reactions.

The chemically-treated solid oxide of this invention is formed generally from an inorganic solid oxide having a relatively high porosity that exhibits Lewis acidic or Brønsted acidic behavior. The solid oxide is chemically-treated with an electron-withdrawing component, typically an electron-withdrawing anion, to form an activator-support.

According to one aspect of the present invention, the solid oxide used to prepare the chemically-treated solid oxide may have a pore volume greater than about 0.1 cc/g. According to another aspect of the present invention, the solid oxide may have a pore volume greater than about 0.5 cc/g. According to yet another aspect of the present invention, the solid oxide may have a pore volume greater than about 1.0 cc/g.

According to another aspect of the present invention, the solid oxide may have a surface area of from about 100 to about 1000 m$^2$/g. According to yet another aspect of the present invention, the solid oxide may have a surface area of from about 200 to about 800 m$^2$/g. According to still another aspect of the present invention, the solid oxide may have a surface area of from about 250 to about 600 m$^2$/g.

The chemically-treated solid oxide may comprise a solid inorganic oxide comprising oxygen and at least one element selected from Group 2, 3, 4, 5, 6, 7, 8, 9, 10, 11, 12, 13, 14, or 15 of the periodic table, or comprising oxygen and at least one element selected from the lanthanide or actinide elements. (See: Hawley's Condensed Chemical Dictionary, 11$^{th}$ Ed., John Wiley & Sons; 1995; Cotton, F. A.; Wilkinson, G.; Murillo; C. A.; and Bochmann; M. Advanced Inorganic Chemistry, 6$^{th}$ Ed., Wiley-Interscience, 1999.) For example, the inorganic oxide may comprise oxygen and at least one element selected from Al, B, Be, Bi, Cd, Co, Cr, Cu, Fe, Ga, La, Mn, Mo, Ni, Sb, Si, Sn, Sr, Th, Ti, V, W, P, Y, Zn or Zr.

Suitable examples of solid oxide materials or compounds that can be used to form the chemically-treated solid oxide include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof. For example, the solid oxide may be silica, alumina, silica-alumina, aluminum phosphate, heteropolytungstates, titania, zirconia, magnesia, boria, zinc oxide, mixed oxides thereof, or any combination thereof.

The solid oxide of this invention encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound. Examples of mixed oxides that can be used in the activator-support of the present invention include, but are not limited to, silica-alumina, silica-titania, silica-zirconia, zeolites, various clay minerals, alumina-titania, alumina-zirconia, zinc-aluminate and the like.

The electron-withdrawing component used to treat the solid oxide may be any component that increases the Lewis or Brønsted acidity of the solid oxide upon treatment (as compared to the solid oxide that is not treated with at least one electron-withdrawing anion). According to one aspect of the present invention, the electron-withdrawing component is an electron-withdrawing anion derived from a salt, an acid, or other compound, such as a volatile organic compound, that may serve as a source or precursor for that anion. Examples of electron-withdrawing anions include, but are not limited to, sulfate, bisulfate, fluoride, chloride, bromide, iodide, fluorosulfate, fluoroborate, phosphate, fluorophosphate, trifluoroacetate, fluorozirconate, fluorotitanate, trifluoroacetate, triflate, and the like, including mixtures and combinations thereof. In addition, other ionic or non-ionic compounds that serve as sources for these electron-withdrawing anions also may be employed in the present invention.

Thus, for example, the chemically-treated solid oxide used with the present invention may be fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, or any combination thereof.

When the electron-withdrawing component comprises a salt of an electron-withdrawing anion, the counterion or cation of that salt may be selected from any cation that allows the salt to revert or decompose back to the acid during calcining. Factors that dictate the suitability of the particular salt to serve as a source for the electron-withdrawing anion include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion include, but are not limited to, ammonium, trialkyl ammonium, tetraalkyl ammonium, tetraalkyl phosphonium, $H^+$, $[H(OEt_2)_2]^+$, and the like.

Further, combinations of one or more different electron-withdrawing anions, in varying proportions, can be used to tailor the specific acidity of the activator-support to the desired level. Combinations of electron-withdrawing components may be contacted with the oxide material simultaneously or individually, and in any order that affords the desired chemically-treated solid oxide acidity. For example, one aspect of this invention is employing two or more electron-withdrawing anion source compounds in two or more separate contacting steps.

Thus, one example of such a process by which a chemically-treated solid oxide is prepared is as follows: a selected solid oxide compound, or combination of oxide compounds, is contacted with a first electron-withdrawing anion source compound to form a first mixture; this first mixture is calcined and then contacted with a second electron-withdrawing anion source compound to form a second mixture; the second mixture is then calcined to form a treated solid oxide compound. In such a process, the first and second electron-withdrawing anion source compounds may be different compounds or the same compound.

According to another aspect of the present invention, the chemically-treated solid oxide may comprise a solid inorganic oxide material, a mixed oxide material, or a combination of inorganic oxide materials, that is chemically-treated with an electron-withdrawing component, and optionally treated with a metal source, including metal salts, metal ions, or other metal-containing compounds. The metal or metal ion may be, for example, zinc, nickel, vanadium, titanium, silver, copper, gallium, tin, tungsten, molybdenum, or any combination thereof. Examples of chemically-treated solid oxides that include a metal or metal ion include, but are not limited to, zinc-impregnated chlorided alumina, titanium-impregnated fluorided alumina, zinc-impregnated fluorided alumina, zinc-impregnated chlorided silica-alumina, zinc-impregnated fluorided silica-alumina, zinc-impregnated sulfated alumina, chlorided zinc aluminate, fluorided zinc aluminate, sulfated zinc aluminate, or any combination thereof.

Any method of impregnating the solid oxide material with a metal may be used. The method by which the oxide is contacted with a metal source, typically a salt or metal-containing compound, may include, but is not limited to, gelling, co-gelling, impregnation of one compound onto another, and the like. If desired, the metal-containing compound may be added to or impregnated into the solid oxide in solution form, and subsequently converted into the supported metal upon calcining. Accordingly, the solid inorganic oxide can further comprise a metal selected from zinc, titanium, nickel, vanadium, silver, copper, gallium, tin, tungsten, molybdenum, or a combination thereof. For example, zinc may be used to impregnate the solid oxide because it provides good catalyst activity and low cost.

The solid oxide may be treated with metal salts or metal-containing compounds before, after, or at the same time that the solid oxide is treated with the electron-withdrawing anion. Following any contacting method, the contacted mixture of oxide compound, electron-withdrawing anion, and the metal ion is typically calcined. Alternatively, a solid oxide material, an electron-withdrawing anion source, and the metal salt or metal-containing compound are contacted and calcined simultaneously.

Various processes may be used to form the chemically-treated solid oxide. The chemically-treated solid oxide may comprise the contact product of at least one solid oxide compound and at least one electron-withdrawing anion source. It is not required that the solid oxide compound be calcined prior to contacting the electron-withdrawing anion source. The contact product may be calcined either during or after the solid oxide compound is contacted with the electron-withdrawing anion source. The solid oxide compound may be calcined or uncalcined. Various processes to prepare solid oxide activator-supports that can be employed in this invention have been reported. For example, such methods are described in U.S. Pat. Nos. 6,107,230, 6,165,929, 6,294,494, 6,300,271, 6,316,553, 6,355,594, 6,376,415, 6,391,816, 6,395,666, 6,524,987, and 6,548,441, each of which is incorporated by reference herein in its entirety.

According to one aspect of the present invention, the solid oxide material may be chemically-treated by contacting it with at least one electron-withdrawing component, typically an electron-withdrawing anion source. Further, the solid oxide material optionally may be chemically treated with a metal ion, and then calcined to form a metal-containing or metal-impregnated chemically-treated solid oxide. According to another aspect of the present invention, the solid oxide material and electron-withdrawing anion source are contacted and calcined simultaneously.

The method by which the oxide is contacted with the electron-withdrawing component, typically a salt or an acid of an electron-withdrawing anion, may include, but is not limited to, gelling, co-gelling, impregnation of one compound onto another, and the like. Thus, following any contacting method, the contacted mixture of the solid oxide, electron-withdrawing anion, and optional metal ion, is calcined.

The solid oxide activator-support (chemically-treated solid oxide) may thus be produced by a process comprising:
1) contacting a solid oxide compound with at least one electron-withdrawing anion source compound to form a first mixture; and
2) calcining the first mixture to form the solid oxide activator-support.

According to another aspect of the present invention, the solid oxide activator-support (chemically-treated solid oxide) may be produced by a process comprising:
1) contacting at least one solid oxide compound with a first electron-withdrawing anion source compound to form a first mixture;
2) calcining the first mixture to produce a calcined first mixture;
3) contacting the calcined first mixture with a second electron-withdrawing anion source compound to form a second mixture; and
4) calcining the second mixture to form the solid oxide activator-support.

According to yet another aspect of the present invention, the chemically-treated solid oxide is produced or formed by contacting the solid oxide with the electron-withdrawing anion source compound, where the solid oxide compound is calcined before, during, or after contacting the electron-withdrawing anion source, and where there is a substantial absence of aluminoxanes and organoborates.

Calcining of the treated solid oxide generally is conducted in an ambient atmosphere, typically in a dry ambient atmosphere, at a temperature of about 200° C. to about 900° C., and for about 1 minute to about 100 hours. Calcining may be conducted at a temperature of from about 300° C. to about 800° C., for example, at a temperature of from about 400° C. to about 700° C. Calcining may be conducted for about 1 hour to about 50 hours, for example, for about 3 hours to about 20 hours. Thus, for example, calcining may be carried out for about 1 to about 10 hours at a temperature of from about 350° C. to about 550° C. Any type of suitable ambient can be used during calcining. Generally, calcining is conducted in an oxidizing atmosphere, such as air. Alternatively, an inert atmosphere, such as nitrogen or argon, or a reducing atmosphere, such as hydrogen or carbon monoxide, may be used.

According to one aspect of the present invention, the solid oxide material may be treated with a source of halide ion, sulfate ion, or a combination of anions, optionally treated with a metal ion, and then calcined to provide the chemically-treated solid oxide in the form of a particulate solid. For example, the solid oxide material may be treated with a source of sulfate (termed a "sulfating agent"), a source of chloride ion (termed a "chloriding agent"), a source of fluoride ion (termed a "fluoriding agent"), or a combination thereof, and calcined to provide the solid oxide activator. Useful acidic activator-supports include, but are not limited to, bromided alumina, chlorided alumina, fluorided alumina, sulfated alumina, bromided silica-alumina, chlorided silica-alumina, fluorided silica-alumina, sulfated silica-alumina, bromided silica-zirconia, chlorided silica-zirconia, fluorided silica-zirconia, sulfated silica-zirconia; a pillared clay, such as a pillared montmorillonite, optionally treated with fluoride, chloride, or sulfate; phosphated alumina or other aluminophosphates optionally treated with sulfate, fluoride, or chloride; or any combination of the above. Further, any of the activator-supports optionally may be treated with a metal ion.

The chemically-treated solid oxide may comprise a fluorided solid oxide in the form of a particulate solid. The fluorided solid oxide may be formed by contacting a solid oxide with a fluoriding agent. The fluoride ion may be added to the oxide by forming a slurry of the oxide in a suitable solvent such as alcohol or water including, but not limited to, the one to three carbon alcohols because of their volatility and low surface tension. Examples of fluoriding agents that may be suitable include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4)_2SiF_6$), ammonium hexafluorophosphate ($NH_4 PF_6$), analogs thereof, and combinations thereof. For example, ammonium bifluoride $NH_4HF_2$ may be used as the fluoriding agent, due to its ease of use and ready availability.

If desired, the solid oxide may be treated with a fluoriding agent during the calcining step. Any fluoriding agent capable of thoroughly contacting the solid oxide during the calcining step can be used. For example, in addition to those fluoriding agents described previously, volatile organic fluoriding agents may be used. Examples of volatile organic fluoriding agents useful in this aspect of the invention include, but are not limited to, freons, perfluorohexane, perfluorobenzene, fluoromethane, trifluoroethanol, and combinations thereof. Gaseous hydrogen fluoride or fluorine itself also can be used with the solid oxide is fluorided during calcining. One convenient method of contacting the solid oxide with the fluoriding agent is to vaporize a fluoriding agent into a gas stream used to fluidize the solid oxide during calcination.

Similarly, in another aspect of this invention, the chemically-treated solid oxide may comprise a chlorided solid oxide in the form of a particulate solid. The chlorided solid oxide may be formed by contacting a solid oxide with a chloriding agent. The chloride ion may be added to the oxide by forming a slurry of the oxide in a suitable solvent. The solid oxide may be treated with a chloriding agent during the calcining step. Any chloriding agent capable of serving as a source of chloride and thoroughly contacting the oxide during the calcining step may be used. For example, volatile organic chloriding agents may be used. Examples of volatile organic chloriding agents that may be suitable include, but are not limited to, certain freons, perchlorobenzene, chloromethane, dichloromethane, chloroform, carbon tetrachloride, trichloroethanol, or any combination thereof. Gaseous hydrogen fluoride or fluorine itself also can be used when the solid oxide is fluorided during calcining. One convenient method of contacting the oxide with the chloriding agent is to vaporize a chloriding agent into a gas stream used to fluidize the solid oxide during calcination.

The amount of fluoride or chloride ion present before calcining the solid oxide may be from about 2 to about 50% by weight, where weight percent is based on the weight of the solid oxide, for example, silica-alumina, before calcining. According to another aspect of this invention, the amount of fluoride or chloride ion present before calcining the solid oxide may be from about 3 to about 25% by weight, and according to another aspect of this invention, may be from about 4 to about 20% by weight. Once impregnated with halide, the halided oxide may be dried by any method known in the art including, but not limited to, suction filtration followed by evaporation, drying under vacuum, spray drying, and the like, although it is also possible to initiate the calcining step immediately without drying the impregnated solid oxide.

The silica-alumina used to prepare the treated silica-alumina typically has a pore volume greater than about 0.5 cc/g. According to one aspect of the present invention, the pore volume may be greater than about 0.8 cc/g, and according to another aspect of the present invention, the pore volume may be greater than about 1.0 cc/g. Further, the silica-alumina may have a surface area greater than about 100 m$^2$/g. According to one aspect of this invention, the surface area may be greater than about 250 m$^2$/g, and according to another aspect of this invention, the surface area may be greater than about 350 m$^2$/g.

The silica-alumina used with the present invention typically has an alumina content from about 5 to about 95%. According to one aspect of this invention, the alumina content of the silica-alumina may be from about 5 to about 50%, and according to another aspect of this invention, the alumina content of the silica-alumina may be from about 8% to about 30% alumina by weight. According to yet another aspect of this invention, the solid oxide component may comprise alumina without silica, and according to another aspect of this invention, the solid oxide component may comprise silica without alumina.

The sulfated solid oxide comprises sulfate and a solid oxide component, such as alumina or silica-alumina, in the form of a particulate solid. Optionally, the sulfated oxide may be treated further with a metal ion such that the calcined sulfated oxide comprises a metal. According to one aspect of the present invention, the sulfated solid oxide comprises sulfate and alumina. In some instances, the sulfated alumina is formed by a process wherein the alumina is treated with a sulfate source, for example, but not limited to, sulfuric acid or a sulfate salt such as ammonium sulfate. This process may be performed by forming a slurry of the alumina in a suitable solvent, such as alcohol or water, in which the desired concentration of the sulfating agent has been added. Suitable organic solvents include, but are not limited to, the one to three carbon alcohols because of their volatility and low surface tension.

According to one aspect of this invention, the amount of sulfate ion present before calcining may be from about 0.5 parts by weight to about 100 parts by weight sulfate ion to about 100 parts by weight solid oxide. According to another aspect of this invention, the amount of sulfate ion present before calcining may be from about 1 part by weight to about 50 parts by weight sulfate ion to about 100 parts by weight solid oxide, and according to still another aspect of this invention, from about 5 parts by weight to about 30 parts by weight sulfate ion to about 100 parts by weight solid oxide. These weight ratios are based on the weight of the solid oxide before calcining. Once impregnated with sulfate, the sulfated oxide may be dried by any method known in the art including, but not limited to, suction filtration followed by evaporation, drying under vacuum, spray drying, and the like, although it is also possible to initiate the calcining step immediately.

The activator-support used to prepare the catalyst compositions of the present invention may be combined with other inorganic support materials, including, but not limited to, zeolites, inorganic oxides, phosphated inorganic oxides, and the like. In one aspect, typical support materials that may be used include, but are not limited to, silica, silica-alumina, alumina, titania, zirconia, magnesia, boria, fluorided alumina, silated alumina, thoria, aluminophosphate, aluminum phosphate, phosphated silica, phosphated alumina, silica-titania, coprecipitated silica/titania, fluorided/silated alumina, and any combination or mixture thereof.

According to yet another aspect of the present invention, one or more of the metallocene compounds may be precontacted with an olefin monomer and an organoaluminum compound for a first period of time prior to contacting this mixture with the activator-support. Once the precontacted mixture of the metallocene compound(s), olefin monomer, and organoaluminum compound is contacted with the activator-support, the composition further comprising the activator-support is termed the "postcontacted" mixture. The postcontacted mixture may be allowed to remain in further contact for a second period of time prior to being charged into the reactor in which the polymerization process will be carried out.

According to yet another aspect of the present invention, the metallocene compound may be precontacted with an olefin monomer and an organoaluminum compound for a first period of time prior to contacting this mixture with the activator-support. Once the precontacted mixture of the metallocene compound, olefin monomer, and organoaluminum compound is contacted with the activator-support, the composition further comprising the activator-support is termed the "postcontacted" mixture. The postcontacted mixture may be allowed to remain in further contact for a second period of time prior to being charged into the reactor in which the polymerization process will be carried out.

3. The Organoaluminum Compound

Organoaluminum compounds that may be used with the present invention include, but are not limited to, compounds having the formula:

$$(R^2)_3Al;$$

where $(R^2)$ is an aliphatic group having from 2 to about 10 carbon atoms. For example, $(R^2)$ may be ethyl, propyl, butyl, hexyl, or isobutyl.

Other organoaluminum compounds that may be used in accordance with the present invention include, but are not limited to, compounds having the formula:

$$Al(X^9)_n(X^{10})_{3-n},$$

where $(X^9)$ is a hydrocarbyl having from 1 to about 20 carbon atoms, $(X^{10})$ is an alkoxide or an aryloxide, any one of which having from 1 to about 20 carbon atoms, a halide, or a hydride, and n is a number from 1 to 3, inclusive.

According to one aspect of the present invention, $(X^9)$ is an alkyl having from 1 to about 10 carbon atoms. Examples of $(X^9)$ moieties include, but are not limited to, ethyl, propyl, n-butyl, sec-butyl, isobutyl, hexyl, and the like. According to another aspect of the present invention, $(X^{10})$ may be independently selected from fluoro or chloro. According to yet another aspect of the present invention, $(X^{10})$ may be chloro. In the formula $Al(X^9)_n(X^{10})_{3-n}$, n is a number from 1 to 3 inclusive, and typically, n is 3. The value of n is not restricted to be an integer; therefore, this formula includes sesquihalide compounds or other organoaluminum cluster compounds.

Examples of organoaluminum compounds that may be suitable for use with the present invention include, but are not limited to, trialkylaluminum compounds, dialkylaluminium halide compounds, dialkylaluminum alkoxide compounds, dialkylaluminum hydride compounds, and combinations thereof. Specific examples of organoaluminum compounds that may be suitable include, but are not limited to: trimethylaluminum (TMA), triethylaluminum (TEA), tripropylaluminum, diethylaluminum ethoxide, tributylaluminum, diisobutylaluminum hydride, triisobutylaluminum, and diethylaluminum chloride.

One aspect of the present invention contemplates precontacting the metallocene compound with at least one organoaluminum compound and an olefin monomer to form a precontacted mixture, prior to contacting this precontacted mixture with the activator-support to form the active catalyst. When the catalyst composition is prepared in this manner, typically, though not necessarily, a portion of the organoaluminum compound is added to the precontacted mixture and another portion of the organoaluminum compound is added to the postcontacted mixture prepared when the precontacted mixture is contacted with the solid oxide activator. However, the entire organoaluminum compound may be used to prepare the catalyst in either the precontacting or postcontacting step. Alternatively, all the catalyst components may be contacted in a single step.

Further, more than one organoaluminum compound may be used in either the precontacting or the postcontacting step. When an organoaluminum compound is added in multiple steps, the amounts of organoaluminum compound disclosed herein include the total amount of organoaluminum compound used in both the precontacted and postcontacted mixtures, and any additional organoaluminum compound added to the polymerization reactor. Therefore, total amounts of organoaluminum compounds are disclosed regardless of whether a single organoaluminum compound or more than one organoaluminum compound is used.

4. The Optional Aluminoxane Cocatalyst

The present invention further provides a catalyst composition comprising an optional aluminoxane cocatalyst. As used herein, the term "aluminoxane" refers to aluminoxane compounds, compositions, mixtures, or discrete species, regardless of how such aluminoxanes are prepared, formed, or otherwise provided. For example, a catalyst composition comprising an optional aluminoxane cocatalyst can be prepared in which aluminoxane is provided as the poly(hydrocarbyl aluminum oxide), or in which aluminoxane is provided as the combination of an aluminum alkyl compound and a source of active protons such as water. Aluminoxanes are also referred to as poly(hydrocarbyl aluminum oxides) or organoaluminoxanes.

The other catalyst components typically are contacted with the aluminoxane in a saturated hydrocarbon compound solvent, though any solvent that is substantially inert to the reactants, intermediates, and products of the activation step may be used. The catalyst composition formed in this manner may be collected by methods known to those of skill in the art including, but not limited to, filtration. Alternatively, the catalyst composition may be introduced into the polymerization reactor without being isolated.

The aluminoxane compound of this invention may be an oligomeric aluminum compound comprising linear structures, cyclic, or cage structures, or mixtures of all three. Cyclic aluminoxane compounds having the formula:

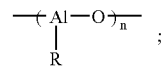

wherein R is a linear or branched alkyl having from 1 to 10 carbon atoms, and n is an integer from 3 to about 10, are encompassed by this invention. The $(AlRO)_n$ moiety shown here also constitutes the repeating unit in a linear aluminoxane. Thus, linear aluminoxanes having the formula:

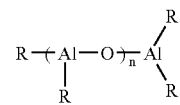

wherein R is a linear or branched alkyl having from 1 to 10 carbon atoms, and n is an integer from 1 to about 50, are also encompassed by this invention.

Further, aluminoxanes also may have cage structures of the formula $R^t_{5m+\alpha}R^b_{m-\alpha}Al_{4m}O_{3m}$, wherein m is 3 or 4 and $\alpha$ is $=n_{Al(3)}-n_{O(2)}+n_{O(4)}$, wherein $n_{Al(3)}$ is the number of three coordinate aluminum atoms, $n_{O(2)}$ is the number of two coordinate oxygen atoms, $n_{O(4)}$ is the number of 4 coordinate oxygen atoms, $R^t$ is a terminal alkyl group, and $R^b$ is a bridging alkyl group, and R is a linear or branched alkyl having from 1 to 10 carbon atoms.

Thus, aluminoxanes that may serve as optional cocatalysts in this invention are represented generally by formulas such as $(R-Al-O)_n$, $R(R-Al-O)_nAlR_2$, and the like, wherein the R group is typically a linear or branched $C_1-C_6$ alkyl such as methyl, ethyl, propyl, butyl, pentyl, or hexyl, and n typically represents an integer from 1 to about 50. Examples of aluminoxane compounds that may be used in accordance with the present invention include, but are not limited to, methylaluminoxane, ethylaluminoxane, n-propylaluminoxane, iso-propylaluminoxane, n-butylaluminoxane, butylaluminoxane, sec-butylaluminoxane, iso-butylaluminoxane, 1-pentylaluminoxane, 2-pentylaluminoxane, 3-pentylaluminoxane, iso-pentylaluminoxane, neopentylaluminoxane, or any combination thereof. Methyl aluminoxane, ethyl aluminoxane, and isobutyl aluminoxane are prepared from trimethylaluminum, triethylaluminum, or triisobutylaluminum, respectively, and sometimes are referred to as poly(methyl aluminum oxide), poly(ethyl aluminum oxide), and poly(isobutyl aluminum oxide), respectively. It is also within the scope of the invention to use an aluminoxane in combination with a trialkylaluminum, such as that disclosed in U.S. Pat. No. 4,794,096, incorporated herein by reference in its entirety.

The present invention contemplates many values of n in the aluminoxane formulas $(R-Al-O)_n$ and $R(R-Al-O)_n$ $AlR_2$, and n typically may be at least about 3. However, depending upon how the organoaluminoxane is prepared, stored, and used, the value of n may vary within a single sample of aluminoxane, and such combinations of organoaluminoxanes are contemplated hereby.

In preparing the catalyst composition of this invention comprising an optional aluminoxane, the molar ratio of the aluminum in the aluminoxane to the metallocene in the composition may be from about 1:10 to about 100,000:1, for example, from about 5:1 to about 15,000:1. The amount of optional aluminoxane added to a polymerization zone may be from about 0.01 mg/L to about 1000 mg/L, from about 0.1 mg/L to about 100 mg/L, or from about 1 mg/L to about 50 mg/L.

Organoaluminoxanes may be prepared by various procedures that are well known in the art. Examples of organoaluminoxane preparations are disclosed in U.S. Pat. Nos. 3,242,099 and 4,808,561, each of which is incorporated by reference herein in its entirety. For example, water in an inert organic solvent may be reacted with an aluminum alkyl compound such as $AlR_3$ to form the desired organoaluminoxane compound. While not intending to be bound by this statement, it is believed that this synthetic method can afford a mixture of both linear and cyclic $(R—Al—O)_n$ aluminoxane species, both of which are encompassed by this invention. Alternatively, organoaluminoxanes may be prepared by reacting an aluminum alkyl compound, such as $AlR_3$ with a hydrated salt, such as hydrated copper sulfate, in an inert organic solvent.

5. The Optional Organoboron Cocatalyst

The present invention further provides a catalyst composition comprising an optional organoboron cocatalyst. The organoboron compound may comprise neutral boron compounds, borate salts, or any combination thereof. For example, the organoboron compounds of this invention may comprise a fluoroorgano boron compound, a fluoroorgano borate compound, or a combination thereof.

Any fluoroorgano boron or fluoroorgano borate compound known in the art can be utilized with the present invention. Examples of fluoroorgano borate compounds that may be used as cocatalysts in the present invention include, but are not limited to, fluorinated aryl borates such as N,N-dimethylanilinium tetrakis-(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, and the like, including mixtures thereof. Examples of fluoroorgano boron compounds that can be used as cocatalysts in the present invention include, but are not limited to, tris(pentafluorophenyl)boron, tris[3,5-bis(trifluoromethyl)phenyl]boron, and the like, including mixtures thereof. Although not intending to be bound by the following theory, these examples of fluoroorgano borate and fluoroorgano boron compounds, and related compounds, are thought to form "weakly-coordinating" anions when combined with organometal compounds, as disclosed in U.S. Pat. No. 5,919,983, incorporated herein by reference in its entirety.

Generally, any amount of organoboron compound may be used. According to one aspect of this invention, the molar ratio of the organoboron compound to the metallocene compound in the composition may be from about 0.1:1 to about 10:1. Typically, the amount of the fluoroorgano boron or fluoroorgano borate compound used as a cocatalyst for the metallocenes may be from about 0.5 moles to about 10 moles of boron compound per total moles of the metallocene compounds. According to another aspect of this invention, the amount of fluoroorgano boron or fluoroorgano borate compound may be from about 0.8 moles to about 5 moles of boron compound per total moles of the metallocene compound.

6. The Optional Ionizing Ionic Compound Cocatalyst

The present invention further provides a catalyst composition comprising an optional ionizing ionic compound cocatalyst. An ionizing ionic compound is an ionic compound that can function to enhance the activity of the catalyst composition. While not intending to be bound by theory, it is believed that the ionizing ionic compound may be capable of reacting with a metallocene compound and converting the metallocene into one or more cationic metallocene compounds, or incipient cationic metallocene compounds. Again, while not intending to be bound by theory, it is believed that the ionizing ionic compound may function as an ionizing compound by completely or partially extracting an anionic ligand, possibly a non-$\eta^5$-alkadienyl ligand such as ($X^3$) or ($X^4$), from the metallocene. However, the ionizing ionic compound is an activator regardless of whether it ionizes the metallocene, abstracts an ($X^3$) or ($X^4$) ligand in a fashion as to form an ion pair, weakens the metal-($X^3$) or metal-($X^4$) bond in the metallocene, simply coordinates to an ($X^3$) or ($X^4$) ligand, or activates the metallocene by some other mechanism.

Further, it is not necessary that the ionizing ionic compound activate the metallocenes only. The activation function of the ionizing ionic compound is evident in the enhanced activity of catalyst composition as a whole, as compared to a catalyst composition containing catalyst composition that does not comprise any ionizing ionic compound. It is also not necessary that the ionizing ionic compound activate each of the metallocene compounds present, nor is it necessary that it activate the any of the metallocene compounds to the same extent.

Examples of ionizing ionic compounds include, but are not limited to, the following compounds: tri(n-butyl)ammonium tetrakis(p-tolyl)borate, tri(n-butyl)ammonium tetrakis (m-tolyl)borate, tri(n-butyl)ammonium tetrakis(2,4-dimethyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethylphenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(m-tolyl)borate, triphenylcarbenium tetrakis(m-tolyl) borate, triphenylcarbenium tetrakis(2,4-dimethylphenyl)borate, triphenylcarbenium tetrakis(3,5-dimethylphenyl) borate, triphenylcarbenium tetrakis[3,5-bis(trifluoromethyl) phenyl]borate, triphenylcarbenium tetrakis (pentafluorophenyl)borate, tropylium tetrakis(p-tolyl) borate, tropylium tetrakis(m-tolyl)borate, tropylium tetrakis (2,4-dimethylphenyl)borate, tropylium tetrakis(3,5-dimethylphenyl)borate, tropylium tetrakis[3,5-bis (trifluoromethyl)phenyl]borate, tropylium tetrakis (pentafluorophenyl)borate, lithium tetrakis (pentafluorophenyl)borate, lithium tetrakis(phenyl)borate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetrakis (phenyl) borate, sodium tetrakis(p-tolyl)borate, sodium tetrakis(m-tolyl)borate, sodium tetrakis(2,4-dimethylphenyl) borate, sodium tetrakis-(3,5-dimethylphenyl)borate, sodium tetrafluoroborate, potassium tetrakis(pentafluorophenyl)borate, potassium tetrakis(phenyl)borate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, tri(n-butyl)ammonium tetrakis(p-tolyl)aluminate, tri(n-butyl)ammonium tetrakis(m-tolyl)aluminate, tri(n-butyl)ammonium tetrakis(2,4-dimethyl)aluminate, tri(n-butyl)ammonium tetrakis(3,5-dimethylphenyl)aluminate, tri(n-butyl)ammonium tetrakis(pentafluorophenyl)aluminate, N,N-dimethylanilinium tetrakis(p-tolyl)aluminate, N,N-dimethylanilinium tetrakis(m-tolyl)aluminate, N,N-dimethylanilinium tetrakis(2,4-dimethylphenyl)aluminate, N,N-dimethylanilinium tetrakis(3,5-dimethylphenyl)aluminate, N,N-dimethylanilinium tetrakis (pentafluorophenyl)aluminate, triphenylcarbenium tetrakis(p-tolyl)aluminate, triphenylcarbenium tetrakis(m-tolyl)aluminate, triphenylcarbenium tetrakis(2,4-dimethylphenyl)aluminate, triphenylcarbenium tetrakis(3,5-dimethylphenyl)aluminate, triphenylcarbenium tetrakis(pentafluorophenyl)aluminate, tropylium tetrakis(p-tolyl)aluminate, tropylium tetrakis(m-tolyl)aluminate, tropylium tetrakis(2,4-dimethylphenyl)aluminate, tropylium tetrakis(3,5-dimethylphenyl)aluminate, tropylium tetrakis (pentafluorophenyl)aluminate, lithium tetrakis(pentafluorophenyl)aluminate, lithium tetrakis(phenyl)aluminate, lithium tetrakis(m-tolyl)aluminate, lithium tetrakis(m-tolyl) aluminate, lithium tetrakis(2,4-dimethylphenyl)aluminate, lithium tetrakis(3,5-dimethylphenyl)aluminate, lithium tetrafluoroaluminate, sodium tetrakis(pentafluorophenyl)aluminate, sodium tetrakis(phenyl)aluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetrakis(phenyl)aluminate, potassium tetrakis(p-tolyl)aluminate, potassium tetrakis(m-tolyl)aluminate, potassium tetrakis(2,4-dimethylphenyl)aluminate, potassium tetrakis (3,5-dimethylphenyl)aluminate, potassium tetrafluoroaluminate, and the like. However, the optional ionizing ionic compounds that are useful in this invention are not limited to these. Other examples of ionizing ionic compounds are disclosed in U.S. Pat. Nos. 5,576,259 and 5,807,938, each of which is incorporated herein by reference in its entirety.

B. Olefin Monomer

Unsaturated reactants that may be useful with catalyst compositions and polymerization processes of this invention include olefin compounds having from about 2 to about 30 carbon atoms per molecule and at least one olefinic double bond. This invention encompasses homopolymerization processes using a single olefin such as ethylene or propylene, as well as copolymerization reactions with at least one different olefinic compound. The resulting copolymer may comprise a major amount of ethylene (>50 mole percent) and a minor amount of comonomer<50 mole percent), though this is not a requirement. The comonomers that may be copolymerized with ethylene typically may have from three to about 20 carbon atoms in their molecular chain.

Acyclic, cyclic, polycyclic, terminal (a), internal, linear, branched, substituted, unsubstituted, functionalized, and non-functionalized olefins may be employed in this invention. For example, typical unsaturated compounds that may be polymerized with the catalysts of this invention include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes, the four normal nonenes, the five normal decenes, and mixtures of any two or more thereof.

Cyclic and bicyclic olefins, including but not limited to, cyclopentene, cyclohexene, norbornylene, norbornadiene, and the like, also may be polymerized as described above.

When a copolymer is desired, the monomer ethylene may be copolymerized with a comonomer. Examples of the comonomer include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes, the four normal nonenes, or the five normal decenes. According to one aspect of the present invention, the comonomer may be selected from 1-butene, 1-pentene, 1-hexene, 1-octene, 1-decene, or styrene.

The amount of comonomer introduced into a reactor zone to produce the copolymer generally may be from about 0.01 to about 50 weight percent comonomer based on the total weight of the monomer and comonomer. According to another aspect of the present invention, the amount of comonomer introduced into a reactor zone may be from about 0.01 to about 40 weight percent comonomer based on the total weight of the monomer and comonomer. According to still another aspect of the present invention, the amount of comonomer introduced into a reactor zone may be from about 0.1 to about 35 weight percent comonomer based on the total weight of the monomer and comonomer. Alternatively, the amount of comonomer introduced into a reactor zone may be any amount sufficient to provide the above concentrations by weight.

While not intending to be bound by this theory, where branched, substituted, or functionalized olefins are used as reactants, it is believed that steric hindrance may impede and/or slow the polymerization process. Thus, branched and/or cyclic portion(s) of the olefin removed somewhat from the carbon—carbon double bond would not be expected to hinder the reaction in the way that the same olefin substituents situated more proximate to the carbon—carbon double bond might. According to one aspect of the present invention, at least one reactant for the catalyst compositions of this invention may be ethylene, so the polymerizations are either homopolymerizations or copolymerizations with a different acyclic, cyclic, terminal, internal, linear, branched, substituted, or unsubstituted olefin. In addition, the catalyst compositions of this invention may be used in the polymerization of diolefin compounds including, but not limited to, 1,3-butadiene, isoprene, 1,4-pentadiene, and 1,5-hexadiene.

C. Preparation of the Catalyst Composition

The present invention encompasses a catalyst composition comprising the contact product of an ansa-metallocene compound, an activator-support, and an organoaluminum compound. This invention further encompasses methods of making the catalyst composition encompassing contacting an ansa-metallocene compound, an activator-support, and an organoaluminum compound, in any order. According to such methods, an active catalyst composition is obtained when the catalyst components are contacted in any sequence or order.

The metallocene compound may be precontacted with an olefinic monomer if desired, not necessarily the olefin monomer to be polymerized, and an organoaluminum cocatalyst for a first period of time prior to contacting this precontacted mixture with the activator-support. The first period of time for contact, the precontact time, between the metallocene compound, the olefinic monomer, and the organoaluminum compound typically may range from about 0.1 hour to about 24 hours, for example, from about 0.1 to about 1 hour. Precontact times from about 10 minutes to about 30 minutes are also typical.

Once the precontacted mixture of the metallocene, olefin monomer, and organoaluminum cocatalyst is contacted with the activator-support, this composition (further comprising the activator-support) is termed the "postcontacted mixture". The postcontacted mixture optionally may be allowed to remain in contact for a second period of time, the postcontact time, prior to initiating the polymerization process. Postcontact times between the precontacted mixture and the activator-support may range in time from about 0.1 hour to about 24 hours, for example, from about 0.1 hour to about 1 hour. The precontacting, the postcontacting step, or both may increase the productivity of the polymer as compared to the same catalyst composition that is prepared without precontacting or postcontacting. However, neither a precontacting step nor a postcontacting step is required.

The postcontacted mixture may be heated at a temperature and for a duration sufficient to allow adsorption, impregnation, or interaction of precontacted mixture and the activator-support, such that a portion of the components of the precontacted mixture is immobilized, adsorbed, or deposited thereon. Where heating is used, the postcontacted mixture may be heated from between about 0° F. to about 150° F. (about minu 20° C. to about 65° C.), for example, from about 40° F. to about 95° F. (about 4° C. to about 35° C.). According to one aspect of this invention, the molar ratio of the total moles of the metallocene compound to the organoaluminum compound may be from about 1:1 to about 1:10,000. According to another aspect of this invention, the molar ratio of the total moles of the metallocene compound to the organoaluminum compound may be from about 1:1 to about 1:1,000. According to yet another aspect of this invention, the molar ratio of the total moles of the metallocene compound to the organoaluminum compound may be from about 1:1 to about 1:100. These molar ratios reflect the ratio of the metallocene compound to the total amount of organoaluminum compound in both the precontacted mixture and the postcontacted mixture combined.

When a precontacting step is used, the molar ratio of olefin monomer to total moles of metallocene compound in the precontacted mixture may be from about 1:10 to about 100,000:1, for example, from about 10:1 to about 1,000:1.

The weight ratio of the activator-support to the organoaluminum compound may be from about 1:5 to about 1,000:1. The weight ratio of the activator-support to the organoaluminum compound may be from about 1:3 to about 100:1, for example, from about 1:1 to about 50:1.

According to a further aspect of this invention, the weight ratio of the total moles of the metallocene compound to the activator-support may be from about 1:1 to about 1:1,000,000. According to yet another aspect of this invention, the weight ratio of the total moles of the metallocene compound to the activator-support may be from about 1:10 to about 1:10,000. According to still another aspect of this invention, the weight ratio of the total moles of the metallocene compound to the activator-support may be from about 1:20 to about 1:1000.

Aluminoxane compounds are not required to form the catalyst composition of the present invention. Thus, the polymerization proceeds in the absence of aluminoxanes. Accordingly, the present invention may use $AlR_3$-type organoaluminum compounds and an activator-support in the absence of aluminoxanes. While not intending to be bound by theory, it is believed that the organoaluminum compound likely does not activate the metallocene catalyst in the same manner as an organoaluminoxane. As a result, the present invention results in lower polymer production costs.

Additionally, no expensive borate compounds or $MgCl_2$ are required to form the catalyst composition of this invention. Nonetheless, aluminoxanes, organoboron compounds, ionizing ionic compounds, organozinc compounds, $MgCl_2$, or any combination thereof optionally may be used in the catalyst composition of this invention. Further, cocatalysts such as aluminoxanes, organoboron compounds, ionizing ionic compounds, organozinc compounds, or any combination thereof optionally may be used as cocatalysts with the metallocene compound, either in the presence or in the absence of the activator-support, and either in the presence or in the absence of the organoaluminum compound.

According to one aspect of this invention, the catalyst activity of the catalyst of this invention may be greater than or equal to about 100 grams polyethylene per gram of chemically-treated solid oxide per hour (abbreviated gP/(gCTSO·hr)). According to another aspect of this invention, the catalyst of this invention may be characterized by an activity of greater than or equal to about 250 gP/(gCTSO·hr). According to still another aspect of this invention, the catalyst of this invention may be characterized by an activity of greater than or equal to about 500 gP/(gCTSO·hr). According to yet another aspect of this invention, the catalyst of this invention may be characterized by an activity of greater than or equal to about 1000 gP/(gCTSO·hr). According to a further aspect of this invention, the catalyst of this invention may be characterized by an activity of greater than or equal to about 2000 gP/(gCTSO·hr). This activity is measured under slurry polymerization conditions using isobutane as the diluent, at a polymerization temperature of about 80–90° C. and a total pressure (ethylene and isobutane) of about 450–550 psig. The reactor should have substantially no indication of any wall scale, coating, or other forms of fouling upon making these measurements.

Any combination of the metallocene compound, the activator-support, the organoaluminum compound, and the olefin monomer, may be precontacted. When any precontacting occurs with an olefinic monomer, it is not necessary that the olefin monomer used in the precontacting step be the same as the olefin to be polymerized. Further, when a precontacting step among any combination of the catalyst components is employed for a first period of time, this precontacted mixture may be used in a subsequent postcontacting step between any other combination of catalyst components for a second period of time. For example, all the catalyst components and 1-hexene may be used in a precontacting step for a first period of time, and this precontacted mixture may then be contacted with the activator-support to form a postcontacted mixture that is contacted for a second period of time prior to initiating the polymerization reaction. For example, the first period of time for contact, the precontact time, between any combination of the metallocene compound, the olefinic monomer, the activator-support, and the organoaluminum compound may be from about 0.1 hour to about 24 hours, for example, from about 0.1 to about 1 hour. Precontact times from about 10 minutes to about 30 minutes are also typical. The postcontacted mixture optionally may be allowed to remain in contact for a second period of time, the postcontact time, prior to initiating the polymerization process. According to one aspect of this invention, postcontact times between the precontacted mixture and any remaining catalyst components may be from about 0.1 hour to about 24 hours, for example, from about 0.1 hour to about 1 hour.

D. Use of the Catalyst Composition in Polymerization Processes

After catalyst activation, the catalyst composition is used to homopolymerize ethylene or copolymerize ethylene with a comonomer.

The polymerization temperature may be from about 60° C. to about 280° C., for example, from about 70° C. to about 110° C. The polymerization reaction typically begins in an inert atmosphere substantially free of oxygen and under substantially anhydrous conditions. For example, a dry, inert atmosphere such as dry nitrogen or dry argon may be used.

The polymerization reaction pressure may be any pressure that does not terminate the polymerization reaction, and is typically a pressure higher than the pretreatment pressures. According to one aspect of the present invention, the polymerization pressure may be from about atmospheric pressure to about 1000 psig. According to another aspect of the present invention, the polymerization pressure may be from about 50 psig to about 800 psig. Further, hydrogen can be used in the polymerization process of this invention to control polymer molecular weight.

Polymerizations using the catalysts of this invention may be carried out in any manner known in the art. Such processes that may be suitable for use with the present invention include, but are not limited to, slurry polymerizations, gas phase polymerizations, solution polymerizations, and multi-reactor combinations thereof. Thus, any polymerization zone known in the art to produce olefin-containing polymers can be utilized. For example, a stirred reactor may be utilized for a batch process, or a loop reactor or a continuous stirred reactor may be used for a continuous process.

A typical polymerization method is a slurry polymerization process (also known as the particle form process), which is well known in the art and is disclosed, for example, in U.S. Pat. Nos. 3,248,179 and 6,239,235, both of which are incorporated by reference herein in their entirety. Other polymerization methods of the present invention for slurry processes are those employing a loop reactor of the type disclosed in U.S. Pat. No. 3,248,179, incorporated by reference herein in its entirety, and those utilized in a plurality of stirred reactors either in series, parallel, or combinations thereof, where the reaction conditions are different in the different reactors. Suitable diluents used in slurry polymerization are well known in the art and include hydrocarbons that are liquids under reaction conditions. The term "diluent" as used in this disclosure does not necessarily mean an inert material, as this term is meant to include compounds and compositions that may contribute to polymerization process. Examples of hydrocarbons that may be used as diluents include, but are not limited to, cyclohexane, isobutane, n-butane, propane, n-pentane, isopentane, neopentane, and n-hexane. Typically, isobutane may be used as the diluent in a slurry polymerization, as provided by U.S. Pat. Nos. 4,424,341, 4,501,885, 4,613,484, 4,737,280, and 5,597,892, each of which is incorporated by reference herein in its entirety.

Various polymerization reactors are contemplated by the present invention. As used herein, "polymerization reactor" includes any polymerization reactor or polymerization reactor system capable of polymerizing olefin monomers to produce homopolymers or copolymers of the present invention. Such reactors may be slurry reactors, gas-phase reactors, solution reactors, or any combination thereof. Gas phase reactors may comprise fluidized bed reactors or tubular reactors. Slurry reactors may comprise vertical loops or horizontal loops. Solution reactors may comprise stirred tank or autoclave reactors.

Polymerization reactors suitable for the present invention may comprise at least one raw material feed system, at least one feed system for catalyst or catalyst components, at least one reactor system, at least one polymer recovery system or any suitable combination thereof. Suitable reactors for the present invention further may comprise any one, or combination of, a catalyst storage system, an extrusion system, a cooling system, a diluent recycling system, or a control system. Such reactors may comprise continuous take-off and direct recycling of catalyst, diluent, and polymer. Generally, continuous processes may comprise the continuous introduction of a monomer, a catalyst, and a diluent into a polymerization reactor and the continuous removal from this reactor of a suspension comprising polymer particles and the diluent.

Polymerization reactor systems of the present invention may comprise a single reactor system or multiple reactor systems. Multiple reactor systems can include at least two reactors that may comprise the same type of reactor (i.e. multiple loop reactors or multiple stirred tank reactors) or different types of reactors (i.e. one or more loops connected to one or more gas phase reactors). Multiple reactor systems may comprise reactors connected together to perform polymerization or reactors that are not connected. The polymer may be polymerized in one reactor under one set of conditions, and then transferred to a second reactor for polymerization under a different set of conditions.

According to one aspect of the invention, the polymerization reactor system may comprise at least one loop slurry reactor. Such reactors are known in the art and may comprise vertical or horizontal loops. Such loops may comprise a single loop or a series of loops. Multiple loop reactors may comprise both vertical and horizontal loops. The slurry polymerization is typically performed in an organic solvent that can disperse the catalyst and polymer. Examples of suitable solvents include butane, hexane, cyclohexane, octane, and isobutane. Monomer, solvent, catalyst and any comonomer may be continuously fed to a loop reactor where polymerization occurs. Polymerization may occur at low temperatures and pressures. Reactor effluent may be flashed to remove the solid resin.

According to yet another aspect of this invention, the polymerization reactor may comprise at least one gas phase reactor. Such systems may employ a continuous recycle stream containing one or more monomers continuously cycled through the fluidized bed in the presence of the catalyst under polymerization conditions. The recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone.

According to still another aspect of the invention, the polymerization reactor may comprise a tubular reactor. Tubular reactors may make polymers by free radical initiation, or by employing the catalysts typically used for coordination polymerization. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another aspect of the invention, the polymerization reactor may comprise a solution polymerization reactor. During solution polymerization, the monomer is contacted with the catalyst composition by suitable stirring or other means. A carrier comprising an inert organic diluent or excess monomer may be employed. If desired, the monomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed during polymerization to obtain better temperature control and to maintain uniform polymerization mixtures throughout the polymerization zone. Adequate means are utilized for dissipating the exothermic heat of polymerization. The polymerization may be effected in a batch manner, or in a continuous manner. The reactor may comprise a series of at least one separator that employs high pressure and low pressure to separate the desired polymer.

According to a further aspect of the invention, the polymerization reactor system may comprise the combination of two or more reactors. Production of polymers in multiple reactors may include several stages in at least two separate polymerization reactors interconnected by a transfer device making it possible to transfer the polymers resulting from the first polymerization reactor into the second reactor. The desired polymerization conditions in one of the reactors may be different from the operating conditions of the other reactors. Alternatively, polymerization in multiple reactors may include the manual transfer of polymer from one reactor to subsequent reactors for continued polymerization. Such reactors may include any combination including, but not limited to, multiple loop reactors, multiple gas reactors, a combination of loop and gas reactors, a combination of autoclave reactors or solution reactors with gas or loop reactors, multiple solution reactors, or multiple autoclave reactors.

After the polymer is produced, it may be formed into various articles, including but not limited to, household containers, utensils, film products, drums, fuel tanks, pipes, geomembranes, and liners. Various processes may be used to form these articles. Usually, additives and modifiers are added to the polymer in order to provide desired effects. By using the invention described herein, articles can likely be produced at a lower cost, while maintaining most or all of the unique properties of polymers produced with metallocene catalysts.

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may be suggested to one of ordinary skill in the art without departing from the spirit of the present invention or the scope of the appended claims.

EXAMPLE 1

Preparation of $Me_2CCp(3-PrInd)ZrCl_2$ (I-1)

BuLi (10.5 mL, 10 M in hexanes, 105 mmol) was added dropwise to 3-propylindene (15.8 g, 100 mmol) dissolved in THF (200 mL) at −78° C. The resulting mixture was warmed to room temperature and stirred overnight. The PrIndLi solution was added dropwise at 0° C. to the fulvene (13.1 g, 124 mmol) prepared by the method described by Stone and Little in *J. Org. Chem.* 1984, 49, 1849. The resulting mixture was stirred at room temperature overnight. The reaction was quenched with water. The mixture from above was extracted with $Et_2O$. The resulting organic layer was washed with water and then dried over anhydrous $Na_2SO_4$. Removal of the solvent produced a viscous brown oil (crude product). The crude product was purified by column chromatography on silica gel with heptane. The pure ligand (20.2 g, 76.5% yield) was obtained as a yellow oil. [Note: 1) the reaction was not optimized; 2) the product was a mixture of the isomers.]

The ligand (5.15 g, 19.5 mmol) was dissolved in 200 mL of anhydrous $Et_2O$ and cooled to 0° C. under nitrogen. n-BuLi (4.1 mL, 10 M in hexanes, 41 mmol) was added dropwise to the ligand solution. The resulting mixture was warmed to room temperature and stirred for an additional 8 hours, giving rise to a red solution. The above solution was added dropwise to $ZrCl_4$ (4.77 g, 20.5 mmol) suspended in a mixture of pentane (200 mL) and $Et_2O$ (20 mL) at 0° C. The resulting mixture was warmed to room temperature and stirred overnight, giving rise to yellow-brown suspension. The solid was separated by centrifuge and extracted with 150 mL of $CH_2Cl_2$. Removal of the solvent from the $CH_2Cl_2$ extract gave an orange solid (4.6 g, 55.6% yield).

$Me_2CCp(3-PrInd)ZrCl_2$ (I-1): $^1H$ NMR (300 MHz, $CDCl_3$) δ 7.62 (d, J=9.0 Hz, 1H), 7.54 (d, J=9.0 Hz, 1H), 7.31 (dd, J=8.1 Hz, 6.9 Hz, 1H), 6.98–7.03 (ddd, J=8.7 Hz, 6.6 Hz, 0.9 Hz, 1H), 6.48–6.57 (m, 2H), 5.83 (q, J=3 Hz, 1H), 5.78 (s, 1H), 5.54 (q, J=3 Hz, 1H), 2.73–2.94 (m, 2H), 2.21 (s, 3H), 1.95 (s, 3H), 1.59–1.72 (m, 2H), 0.98 (t, J=8.1 Hz, 3H); $^{13}C$ NMR (75 MHz, $CDCl_3$) δ 129.22, 126.58, 126.09, 125.68, 124.27, 123.51, 120.88, 120.37, 120.15, 118.97, 113.52, 105.76, 104.18, 99.58, 39.93, 30.51, 27.46, 26.68, 24.63, 15.33.

EXAMPLE 2

Preparation of $Me_2CCp(3-ButenylInd)ZrCl_2$ (I-2)

$Me_2CCp(3-ButenylInd)ZrCl_2$ was prepared in the same manner as I-1 except using butenylindene instead of propylindene. $Me_2CCp(3-ButenylInd)ZrCl_2$ (I-2): $^1H$ NMR (300 MHz, $CDCl_3$) δ 7.61 (dt, J=8.7 Hz, 0.9 Hz, 1H), 7.53 (dt, J=8.7 Hz, 0.9 Hz, 1H), 7.28–7.34 (ddd, J=8.7 Hz, 6.6 Hz, 0.9 Hz, 1H), 6.98–7.03 (ddd, J=8.7 Hz, 6.6 Hz, 1.2 Hz, 1H), 6.48–6.57 (m, 2H), 5.76–5.89 (m, 2H), 5.78 (s, 1H), 5.52–5.55 (m, 1H), 4.95–5.07 (m, 2H), 2.85–3.02 (m, 2H), 2.32–2.41 (m, 2H), 2.21 (s, 3H), 1.94 (s, 3H); $^{13}C$ NMR (75 MHz, $CDCl_3$) δ 137.06, 128.65, 126.07, 125.26, 124.55, 123.64, 122.95, 120.38, 119.92, 119.56, 118.45, 115.12, 112.92, 105.24, 103.69, 99.15, 39.40, 34.61, 27.49, 26.86, 26.12.

EXAMPLE 3

Preparation of $Me_2CCp(3-Me_3SiInd)ZrCl_2$ (I-3)

$Me_2CCp(3-Me_3SiInd)ZrCl_2$ was prepared in the same manner as I-1 except using trimethylsilylindene instead of propylindene. $Me_2CCp(3-Me3SiInd)ZrCl_2$ (I-3): $^1H$ NMR (300 MHz, $CDCl_3$) δ 7.79 (dt, J=8.7 Hz, 0.9 Hz, 1H), 7.73 (dt, J=8.7 Hz, 0.9 Hz, 1H), 7.38–7.43 (ddd, J=8.7 Hz, 6.6 Hz, 0.9 Hz, 1H), 7.09–7.15 (ddd, J=8.7 Hz, 6.6 Hz, 1.2 Hz, 1H), 6.48–6.52 (m, 2H), 6.08 (s, 1H), 5.86 (q, J=3 Hz, 1H), 5.75 (q, J=3 Hz, 11H), 2.28 (s, 3H), 2.02 (s, 3H), 0.47 (s, 9H); $^{13}$C NMR (75 MHz, CDCl$_3$) δ 136.89, 126.52, 125.84, 125.68, 123.57, 121.40, 121.06, 120.89, 119.16, 118.80, 118.45, 106.79, 105.76, 102.72, 39.46, 26.51, 26.38, 0.25.

EXAMPLE 4

Preparation of Me$_2$CCp(Ind)ZrCl$_2$ (C-4)

Me$_2$CCp(Ind)ZrCl$_2$ was prepared in the same manner as I-1 except using indene instead of propylindene. Me$_2$CCp(Ind)ZrCl$_2$: $^1$H NMR (300 MHz, CDCl$_3$) δ 7.66 (dq, J=9 Hz, 0.9 Hz, 1H), 7.61 (dt, J=9 Hz, 0.9 Hz, 1H), 7.31–7.36 (ddd, J=9 Hz, 6.6 Hz, 0.9 Hz, 1H), 7.01–7.06 (ddd, J=9 Hz, 6.6 Hz, 0.9 Hz 1H), 6.83 (dd, J=3.6 Hz, 0.6 Hz, 1H), 6.48–6.53 (m, 2H), 6.12 (d, J=3.6 Hz, 1H), 5.83 (q, J=3 Hz, 1H), 5.71 (q, J=3 Hz, 1H), 2.21 (s, 3H), 1.99 (s, 1H); $^{13}$C NMR (75 MHz, CDCl$_3$) δ 130.47, 126.14, 125.97, 125.61, 122.70, 121.19, 120.50, 119.81, 117.90, 113.26, 111.82, 105.89, 103.98, 102.77, 39.58, 26.72, 26.10.

EXAMPLE 5

Preparation of meso-Ph$_2$Si(3-PrInd)$_2$ZrCl$_2$ (I-4)

BuLi (42 mL, 2.5 M in hexanes, 105 mmol) was added dropwise to propylindene (15.8 g, 100 mmol) dissolved in THF (120 mL) at −78° C. The resulting mixture was warmed to room temperature and stirred overnight. The above PrIndLi solution was added dropwise to Ph$_2$SiCl$_2$ (12.65 g, 50 mmol) dissolved in 20 mL of THF at 0° C. The resulting mixture was stirred at room temperature overnight. The reaction was quenched with water. The mixture from above was extracted with Et$_2$O. The resulting organic layer was washed with water and then dried over anhydrous Na$_2$SO$_4$. Removal of the solvent gave a pale yellow solid (crude product). The pure ligand (13.9 g, 56% yield) was obtained as a white solid from recrystallization in pentane. (Note: the reaction was not optimized. Also, the product was a mixture of the isomers).

The ligand (3.72 g, 7.5 mmol) was dissolved in 75 mL of anhydrous Et$_2$O and cooled to −78° C. under nitrogen. n-BuLi (6.6 mL, 2.5 M in hexanes, 16.5 mmol) was added dropwise to the ligand solution. The resulting mixture was warmed to room temperature and stirred overnight. The above Ph$_2$Si(PrIndLi)$_2$ solution was cooled to −78° C. and quickly added to precooled ZrCl$_4$ (1.84 g, 7.9 mmol) suspended in 40 mL toluene at −78° C. The resulting mixture was stirred at −78° C. for an additional 5 min, then slowly warmed to room temperature and stirred overnight. The solvent was removed under vacuum. The residue was extracted with toluene and centrifuged. The supernatant was collected and concentrated. The meso-isomer (1.08 g, 22% yield) was obtained by crystallization in the mixture of toluene and pentane at −10° C. Meso-Ph$_2$Si(3-PrInd)$_2$ZrCl$_2$: $^1$H NMR (300 MHz, CDCl$_3$) δ 8.27–8.30 (m, 2H), 8.07–8.09 (m, 2H), 7.45–7.62 (m, 8H), 7.15–7.20 (m, 4H), 6.72–6.75 (m, 2H), 5.68 (s, 2H), 2.81–2.90 (m, 4H), 1.55–1.75 (m, 4H), 0.98 (t, J=7.2 Hz, 6H); $^{13}$C NMR (75 MHz, CDCl$_3$) δ 135.05, 134.46, 134.27, 133.06, 132.91, 132.38, 131.16, 130.81, 129.50, 128.81, 128.77, 126.79, 126.44, 125.52, 124.00, 119.59, 80.81, 30.55, 23.39, 14.22. The mixture of racemic and meso isomer was collected from the crystallization supernatant.

EXAMPLE 6

Preparation of meso-Me$_2$Si(3-PrInd)$_2$ZrCl$_2$ (I-5)

meso-Me$_2$Si(3-PrInd)$_2$ZrCl$_2$ is prepared in the same manner as 14, except using dichlorodimethylsilane instead of dichlorodiphenylsilane. meso-Me$_2$Si(3-PrInd)$_2$ZrCl$_2$: $^1$H NMR (300 MHz, CDCl$_3$) δ 7.48–7.52 (m, 2H), 7.41–7.44 (m, 2H), 7.13–7.18 (m, 2H), 6.89–6.93 (m, 2H), 5.57 (s, 2H), 2.78–2.88 (m, 4H), 1.55–1.71 (m, 4H), 1.35 (s, 3H), 0.92 (t, J=7.5 Hz, 6H), 0.88 (s, 3H); $^{13}$C NMR (75 MHz, CDCl$_3$) δ 133.00, 132.43, 130.04, 126.22, 126.05, 125.81, 124.11, 117.03, 84.88, 30.52, 23.35, 14.20, −0.97, −2.71.

EXAMPLE 7

Preparation of meso-Ph$_2$Si(3–1-BuInd)$_2$ZrCl$_2$ (I-6)

meso-Ph$_2$Si(3-i-BuInd)$_2$ZrCl$_2$ is prepared in the same manner as I-4, except using iso-butylindene instead of propylindene. meso-Ph$_2$Si(3-i-BuInd)$_2$ZrCl$_2$: $^1$H NMR (300 MHz, CDCl$_3$) δ 8.32–8.35 (m, 2H), 8.09–8.12 (m, 2H), 7.46–7.65 (m, 8H), 7.17–7.24 (m, 4H), 6.72–6.77 (m, 2H), 5.68 (s, 2H), 2.66–2.91 (m, 4H), 1.82–1.98 (m, 2H), 0.99 (d, J=6.9 Hz, 6H), 0.93 (d, J=6.9 Hz, 6H); $^{13}$C NMR (75 MHz, CDCl$_3$) δ 135.10, 134.71, 134.45, 133.06, 132.94, 131.33, 131.22, 130.87, 129.46, 128.85, 128.81, 126.90, 126.81, 125.50, 124.18, 120.33, 80.86, 37.68, 29.74, 23.11, 22.55.

Other Compounds

Cp$_2$ZrCl$_2$ (C-1), Ind$_2$ZrCl$_2$ (C-2), CpIndZrCl$_2$ (C-3), Me$_2$CCpFluZrCl$_2$ (C-5), and Other Metallocene Compounds Referred to Herein Cp$_2$ZrCl$_2$ (C-1), Ind$_2$ZrCl$_2$ (C-2), CpIndZrCl$_2$ (C-3), Me$_2$CCpFluZrCl$_2$ (C-5), and other metallocene compounds referred to herein, including meso-Me$_2$Si(2-MeInd)$_2$ZrCl$_2$, meso-EBIZrCl$_2$, rac-Me$_2$Si(2-MeInd)$_2$ZrCl$_2$, rac-EBIZrCl$_2$, rac-Me$_2$SiInd$_2$ZrCl$_2$, are commercially available.

EXAMPLES 8–17

All polymerization runs were conducted in a 1-gallon (3.785 L) stainless steel reactor. Two liters of isobutane and alkyl aluminum cocatalyst/scavenger were used in all examples. No hydrogen was added in any runs. Comonomer, if used, was 1-hexene. Metallocene solutions (1 mg/mL) were usually prepared by dissolving about 10–20 mg of metallocene in a mixture of about 2–4 mL of hexene, about 2–4 mL of 1 M TIBA or TEA, and about 6–12 mL of heptane. Most preferable was a solution prepared by dissolving about 20 mg of metallocene in a mixture of about 4 mL of hexene, about 4 mL of 1 M TIBA or TEA and about 12 mL of heptane.

Alkyl aluminum, SSA and the metallocene solution were added in the order through a charge port while venting isobutane vapor. The charge port was closed and 2 liters of isobutane were added. The contents of the reactor were stirred and heated to the desired run temperature, and ethylene was then introduced along with the desired amount of hexene (if comonomer was used). Ethylene was fed on demand to maintain the specified pressure for the specified length of the polymerization run. The reactor was maintained at the desired run temperature through the run by an automated heating-cooling system.

Melt index (MI, g/10 min) was determined in accordance with ASTM D1238 condition F at 190° C. with a 2,160 gram weight.

High load melt index (HLMI, g/10 min) was determined in accordance with ASTM D1238 condition E at 190° C. with a 21,600 gram weight.

EXAMPLE 8

Evaluation of Inventive Metallocenes I-1, I-2, I-3

Various polymerization runs (1–15) were conducted to evaluate the efficacy of carbon bridged cyclopentadienyl 3-substituted indenyl metallocenes, in particular, $Me_2CCp(3-PrInd)ZrCl_2$ (I-1), $Me_2CCp(3-ButenylInd)ZrCl_2$ (I-2), and $Me_2CCp(3-Me_3SiInd)ZrCl_2$ (I-3), for preparing low molecular weight, high melt index polyethylene. Comparative polymerization runs (16–20) using metallocenes C-1, C-2, C-3, C-4, and C-5 were also carried out to determine the relative efficacy of the catalyst systems of the present invention. The results are presented in Table 1.

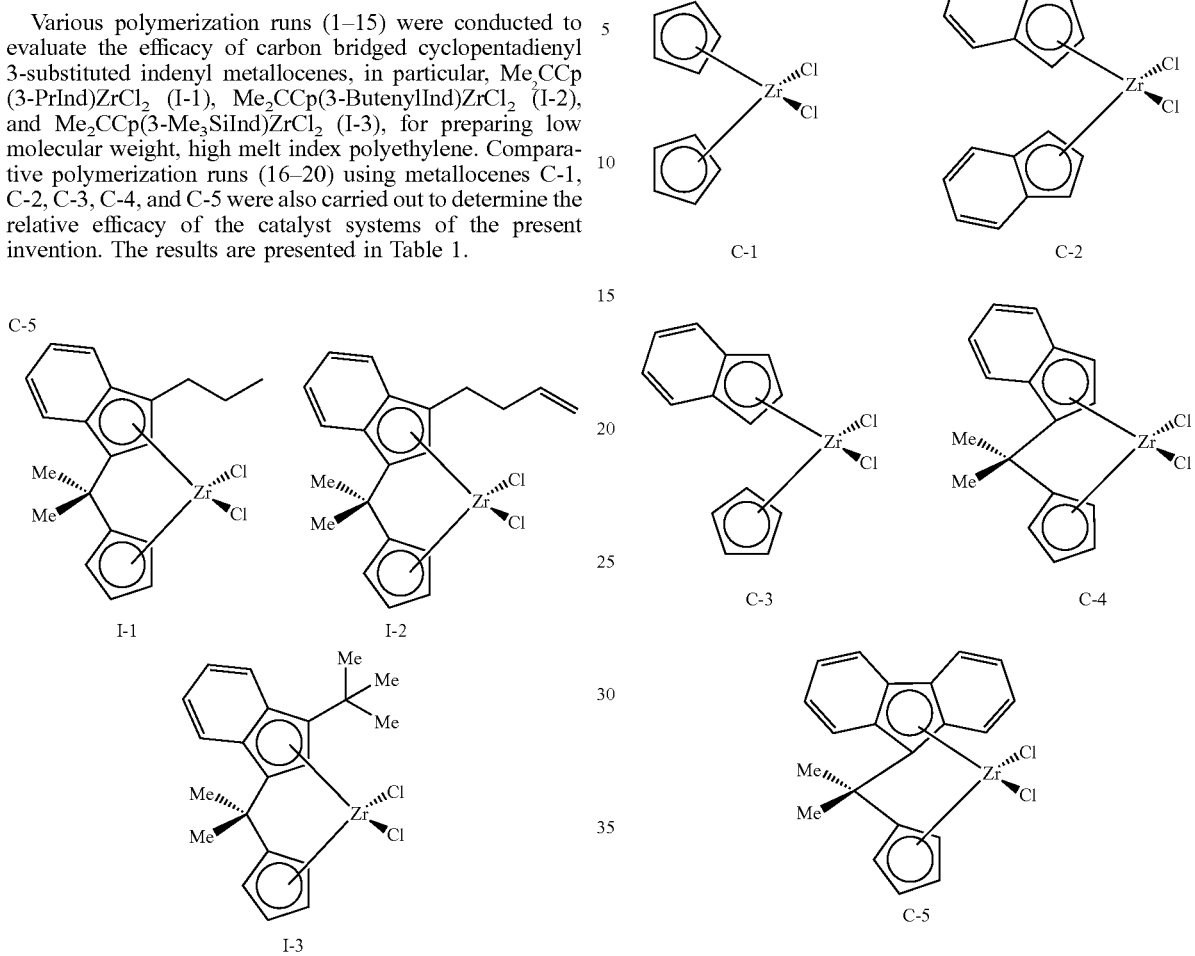

TABLE 1

| Run | Metallocene | Time (min) | Temp (C.) | Pressure (psig) | Comonomer (1-hexene) (g) | Support-Activator Type* | Support-Activator wt (mg) | $R_3Al$ (mmol) | Metallocene Wt. (g) | Solid PE (g) | Metallocene Activity (g/g/hr) | Support-Activator Activity (g/g/hr) | MI |
|---|---|---|---|---|---|---|---|---|---|---|---|---|---|
| 1 | (I-1) | 30 | 80 | 450 | 25 | F-SSA | 100 | (0.5) TIBA | 0.0010 | 395.0 | 790000 | 7900 | 835.0 |
| 2 | (I-1) | 30 | 80 | 450 | 15 | F-SSA | 100 | (0.5) TIBA | 0.0010 | 184.0 | 368000 | 3680 | 495.0 |
| 3 | (I-1) | 30 | 80 | 450 | 5 | F-SSA | 100 | (0.5) TIBA | 0.0010 | 154.0 | 308000 | 3080 | 281.5 |
| 4 | (I-1) | 31 | 80 | 450 | 0 | F-SSA | 100 | (0.5) TIBA | 0.0010 | 62.0 | 120000 | 1200 | 143.6 |
| 5 | (I-1) | 30 | 90 | 450 | 5 | F-SSA | 100 | (0.5) TIBA | 0.0010 | 258.0 | 516000 | 5160 | 828.0 |
| 6 | (I-1) | 30 | 90 | 450 | 0 | F-SSA | 100 | (0.5) TIBA | 0.0010 | 163.0 | 326000 | 3260 | 511.0 |
| 7 | (I-1) | 30 | 90 | 550 | 5 | F-SSA | 100 | (0.5) TIBA | 0.0005 | 352.0 | 1408000 | 7040 | 774.0 |
| 8 | (I-2) | 15 | 80 | 450 | 25 | F-SSA | 200 | (0.5) TIBA | 0.0010 | 224.0 | 896000 | 4480 | 831.0 |
| 9 | (I-2) | 30 | 90 | 550 | 5 | F-SSA | 100 | (1.0) TEA | 0.0005 | 186.0 | 744000 | 3720 | 699.0 |
| 10 | (I-2) | 30 | 80 | 450 | 30 | F-SSA | 100 | (0.5) TIBA | 0.0010 | 353.0 | 706000 | 7060 | 849.0 |
| 11 | (I-2) | 25 | 90 | 550 | 5 | S-SSA | 100 | (0.5) TIBA | 0.0010 | 465.0 | 1116000 | 11160 | 842.0 |
| 12 | (I-2) | 30 | 90 | 550 | 5 | S-SSA | 100 | (0.5) TIBA | 0.0005 | 232.0 | 928000 | 4640 | 646.0 |
| 13 | (I-2) | 30 | 80 | 450 | 30 | S-SSA | 100 | (0.5) TIBA | 0.0020 | 250.0 | 250000 | 5000 | 824.0 |
| 14 | (I-3) | 30 | 80 | 450 | 25 | F-SSA | 100 | (0.5) TIBA | 0.0010 | 171.0 | 342000 | 3420 | 462.0 |
| 15 | (I-3) | 30 | 80 | 450 | 25 | F-SSA | 200 | (0.5) TIBA | 0.0010 | 367.0 | 734000 | 3670 | 428.0 |
| 16 | (C-1) | 30 | 80 | 450 | 25 | F-SSA | 200 | (0.5) TIBA | 0.0010 | 31.0 | 62000 | 310 | 0.0 |
| 17 | (C-2) | 30 | 80 | 450 | 25 | F-SSA | 100 | (0.5) TIBA | 0.0010 | 89.0 | 178000 | 1780 | 0.2 |
| 18 | (C-3) | 30 | 80 | 450 | 25 | F-SSA | 200 | (0.5) TIBA | 0.0005 | 280.0 | 1120000 | 2800 | 0.2 |
| 19 | (C-4) | 30 | 80 | 450 | 25 | F-SSA | 100 | (0.5) TIBA | 0.0010 | 27.0 | 54000 | 540 | 857.0 |
| 20 | (C-5) | 30 | 90 | 550 | 40 | F-SSA | 200 | (1.0) TEA | 0.0010 | 229.4 | 458800 | 2294 | 0.2 |

*F-SSA is fluorided silica-alumina; S-SSA is sulfated alumina

Each of the exemplary inventive catalyst compositions used in runs 1–15 produced polyethylene having a melt index higher than 50, in particular, from about 143 to about 849. Thus, each of the metallocenes I-1, I-2, and I-3 effectively prepared polyethylene having a high melt index without the use of hydrogen.

In runs 16–18, each of the comparative unbridged metallocenes C-1, C-2, and C-3 did not produce a polymer having a melt index above 0.2.

The polymer resulting from metallocene C-4 (run 19) had a high melt index. However, the activity of the metallocene was very poor, which is consistent with the results reported in *Makromol. Chem.* 1992, 193, 1643 and *J Polym. Sci. Part A*, 1994, 32, 2817 (in which the metallocene was activated with MAO), incorporated herein by reference in its entirety.

Another comparative 1-carbon bridged metallocene, C-5, possesses better activity, but produces fractional MI resins under similar conditions (run 20). Advantageously, the catalyst systems of the present invention provide both a high activity and result in high melt index polymers.

EXAMPLE 9

Evaluation of meso-Ph$_2$Si(3-PrInd)$_2$ZrCl$_2$ (I-4)

Various polymerization runs (21–23) were conducted to evaluate the efficacy of meso-Ph$_2$Si(3-PrInd)$_2$ZrCl$_2$ for preparing low molecular weight, high melt index polyethylene. In each instance, 25 g of 1-hexene was used as the comonomer. Fluorided silica-alumina was used as the support-activator.

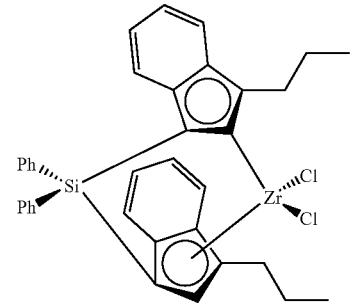

I-4

The results are presented in Table 2.

TABLE 2

| | Polymerization Conditions | | | | | | Results | |
|---|---|---|---|---|---|---|---|---|
| Run | Time (min) | Temperature (C.) | Pressure (psi) | Support-Activator Weight (mg) | TEA (15 wt %) (mL) | Metallocene Weight (g) | Solid PE (g) | MI |
| 21 | 60 | 80 | 450 | 200 | 1.0 | 0.0015 | 258.6 | 316.2 |
| 22 | 60 | 80 | 450 | 200 | 1.0 | 0.0015 | 286.2 | 304.4 |
| 23 | 30 | 90 | 550 | 200 | 1.0 | 0.0015 | 304 | 294 |

Each of runs 21–23 produced polyethylene having a melt index higher than 50, in particular, from about 294 to about 316. Thus, metallocene I-4 effectively prepared polyethylene having a high melt index without the use of hydrogen.

EXAMPLE 10

Evaluation of meso-Me$_2$Si(3-PrInd)$_2$ZrCl$_2$ (I-5)

Various polymerization runs (24–26) were conducted to evaluate the efficacy of meso-Me$_2$Si(3-PrInd)$_2$ZrCl$_2$ for preparing low molecular weight, high melt index polyethylene. In each instance, 25 g of 1-hexene was used as the comonomer. Fluorided silica-alumina was used as the support-activator.

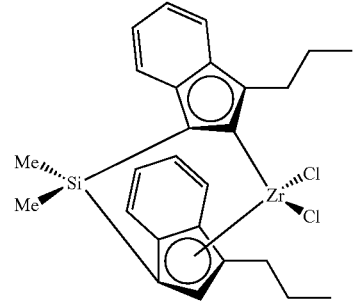

I-5

The results are presented in Table 3.

TABLE 3

| | Polymerization Conditions | | | | | Results | |
| --- | --- | --- | --- | --- | --- | --- | --- |
| Run | Time (min) | Temperature (C.) | Pressure (psi) | Support-Activator Weight (mg) | TEA (15 wt %) (mL) | Metallocene Weight (g) | Solid PE (g) | MI |
| 24 | 60 | 80 | 450 | 200 | 1.0 | 0.0020 | 576.8 | 513.7 |
| 25 | 60 | 80 | 450 | 200 | 1.0 | 0.0012 | 466.6 | 685.0 |
| 26 | 60 | 90 | 550 | 200 | 1.0 | 0.0012 | 612.9 | 274.0 |

Each of runs 24–26 produced polyethylene having a melt index higher than 50, in particular, from about 274 to about 685. Thus, metallocene I-5 effectively prepared polyethylene having a high melt index without the use of hydrogen.

EXAMPLE 11

Evaluation of meso-Ph$_2$Si(3-i-ButylInd)$_2$ZrCl$_2$ (I-6)

Various polymerization runs (27–29) were conducted to evaluate the efficacy of meso-Ph$_2$Si(3-i-ButylInd)$_2$ZrCl$_2$ for preparing low molecular weight, high melt index polyethylene. In each instance, 1-hexene was used as the comonomer. Fluorided silica-alumina was used as the support-activator.

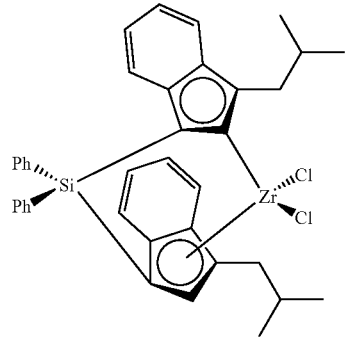

I-6

The results are presented in Table 4.

TABLE 4

| | Polymerization Conditions | | | | | | Results | |
| --- | --- | --- | --- | --- | --- | --- | --- | --- |
| Run | Time (min) | Temperature (C.) | Pressure (psi) | 1-Hexene Weight (g) | Support-Activator Weight (mg) | TEA (15 wt %) (mL) | Metallocene Weight (g) | Solid PE (g) | MI |
| 27 | 60 | 80 | 450 | 25.0 | 200 | 1.0 | 0.0015 | 144.0 | 545.0 |
| 28 | 60 | 90 | 550 | 15.0 | 200 | 1.0 | 0.0015 | 251.0 | High |
| 29 | 60 | 90 | 550 | 40.0 | 200 | 1.0 | 0.0015 | 282.0 | High |

Each of runs 27–29 produced polyethylene having a melt index higher than 50, in particular, from 545 to a melt index that was too high to measure. Thus, metallocene I-6 effectively prepared polyethylene having a high melt index without the use of hydrogen.

EXAMPLE 12

Comparison with rac/meso-Ph$_2$Si(3-PrInd)$_2$ZrCl$_2$

Comparative polymerization runs (30–33) were also carried out to determine the relative efficacy of the corresponding racemic/meso mixture, rac/meso-Ph$_2$Si(3-PrInd)$_2$ZrCl$_2$. The ratio of the racemic to meso isomer was 3:2. In each instance, 1-hexene was used as the comonomer. Fluorided silica-alumina was used as the support-activator. The results are presented in Table 5.

TABLE 5

| | Polymerization Conditions | | | | | | | Results | |
| --- | --- | --- | --- | --- | --- | --- | --- | --- | --- |
| Run | Time (min) | Temperature (C.) | Pressure (psi) | 1-Hexene Weight (g) | Support-Activator Weight (mg) | TEA (15 wt %) (mL) | Metallocene Weight (g) | Solid PE (g) | MI |
| 30 | 60 | 80 | 450 | 25.0 | 200 | 1.0 | 0.0015 | 118.0 | 3.6 |
| 31 | 60 | 80 | 450 | 50.0 | 200 | 1.0 | 0.0015 | 260.0 | 3.7 |
| 32 | 60 | 80 | 450 | 75.0 | 200 | 1.0 | 0.0015 | 333.0 | 4.0 |
| 33 | 60 | 90 | 550 | 25.0 | 200 | 1.0 | 0.0015 | 325.0 | 3.9 |

As is evident from the data presented, the combination of racemic and meso isomers did not produce a melt index as high as the pure meso isomer. Nonetheless, the corresponding racemic isomer of metallocene I-4 did not prepare polyethylene having a melt index greater than 50 without the use of hydrogen.

EXAMPLE 13

Comparison with rac/meso-Me$_2$Si(3-PrInd)$_2$ZrCl$_2$

Comparative polymerization runs (34–36) were carried out to determine the relative efficacy of the corresponding racemic/meso mixture, rac/meso-Me$_2$Si(3-PrInd)$_2$ZrCl$_2$. The ratio of the racemic to meso isomer was 1:2. In each instance, 1-hexene was used as the comonomer. Fluorided silica-alumina was used as the support-activator. The results are presented in Table 6.

TABLE 6

| | Polymerization Conditions | | | | | | | Results | |
| --- | --- | --- | --- | --- | --- | --- | --- | --- | --- |
| Run | Time (min) | Temperature (C.) | Pressure (psi) | 1-Hexene Weight (g) | Support-Activator Weight (mg) | TEA (15 wt %) (mL) | Metallocene Weight (g) | Solid PE (g) | MI |
| 34 | 30 | 80 | 450 | 25.0 | 200 | 1.0 | 0.0015 | 210.0 | 21.3 |
| 35 | 30 | 80 | 450 | 75.0 | 200 | 1.0 | 0.0015 | 360.0 | 28.7 |
| 36 | 60 | 80 | 450 | 25.0 | 200 | 1.0 | 0.0015 | 381.0 | 27.9 |

As is evident from the data presented, the combination of racemic and meso isomers did not produce a melt index as high as the pure meso isomer. Nonetheless, the corresponding racemic isomer of metallocene I-5 did not prepare polyethylene having a melt index greater than 50 without the use of hydrogen.

EXAMPLE 14

Comparison with rac/meso-Ph$_2$Si(3-i-ButylInd)$_2$ZrCl$_2$

A comparative polymerization run (37) was carried out to determine the relative efficacy of the corresponding racemic/meso mixture, rac/meso-Ph$_2$Si(3-i-ButylInd)$_2$ZrCl$_2$. The ratio of the racemic to meso isomer was 2.2:1. 1-hexene was used as the comonomer. Fluorided silica-alumina was used as the support-activator. The results are presented in Table 7.

TABLE 7

| | Polymerization Conditions | | | | | | | Results | |
|---|---|---|---|---|---|---|---|---|---|
| | | | | | Support- | | | | |
| Run | Time (min) | Temperature (C.) | Pressure (psi) | 1-Hexene Weight (g) | Activator Weight (mg) | TEA (15 wt %) (mL) | Metallocene Weight (g) | Solid PE (g) | MI |
| 37 | 30 | 90 | 550 | 25.0 | 200 | 1.0 | 0.0015 | 184.0 | 3.8 |

As is clear from the data provided herein, the combination of racemic and meso isomers did not produce a melt index as high as the pure meso isomer. Nonetheless, the corresponding racemic isomer of metallocene I-6 did not prepare polyethylene having a melt index greater than 50 without the use of hydrogen.

EXAMPLE 15

General Comparison with meso-Me$_2$Si(2-MeInd)$_2$ZrCl$_2$ and rac Me$_2$Si(2-MeInd)$_2$ZrCl$_2$ Comparative polymerization runs (38–43) were carried out to determine the relative efficacy of the metallocene catalyst compositions of the present invention with rac- and meso-silyl bridged bis(2-substituted indenyl)zirconium dichlorides. In each instance, 1-hexene was used as the comonomer. Fluorided silica-alumina was used as the support-activator. The results are presented in Table 8.

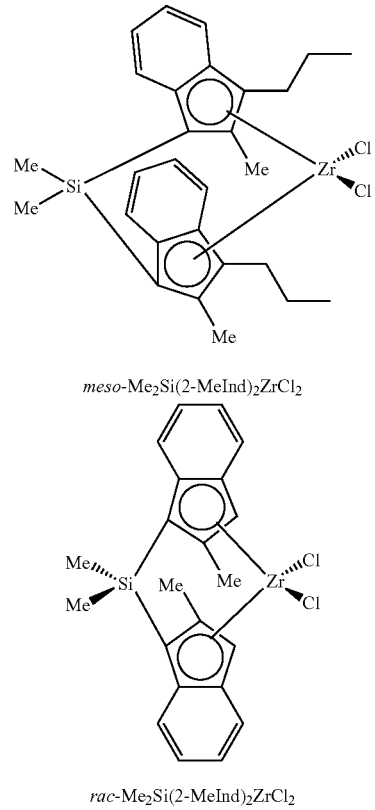

*meso*-Me$_2$Si(2-MeInd)$_2$ZrCl$_2$

*rac*-Me$_2$Si(2-MeInd)$_2$ZrCl$_2$

TABLE 8

| | | Polymerization Conditions | | | | | | | Results | |
|---|---|---|---|---|---|---|---|---|---|---|
| | | | | | | Support- | | | | |
| Run | Metallocene | Time (min) | Temperature (C.) | Pressure (psi) | 1-Hexene Weight (g) | Activator Weight (mg) | TEA (15 wt %) (mL) | Metallocene Weight (g) | Solid PE (g) | MI |
| 38 | meso | 30 | 80 | 450 | 25.0 | 200 | 1.0 | 0.0030 | 84.0 | 0.0 |
| 39 | meso | 60 | 80 | 450 | 25.0 | 200 | 1.0 | 0.0020 | 62.0 | 0.0 |
| 40 | meso | 30 | 80 | 450 | 75.0 | 200 | 1.0 | 0.0030 | 155.8 | 2.9 |
| 41 | racemic | 30 | 80 | 450 | 25.0 | 200 | 1.0 | 0.0020 | 236.1 | 0.0 |
| 42 | racemic | 30 | 80 | 450 | 50.0 | 200 | 1.0 | 0.0020 | 432.7 | 0.0 |
| 43 | racemic | 30 | 90 | 550 | 25.0 | 200 | 1.0 | 0.0020 | 367.8 | 0.0 |

The results indicate that both racemic and meso silyl bridged bis(2-substituted indenyl)zirconium dichlorides provide low melt index polyethylene.

EXAMPLE 16

General Comparison with meso-Me$_2$SiInd$_2$ZrCl$_2$ and rac-Me$_2$SiInd$_2$ZrCl$_2$ Comparative polymerization runs (44–45) were carried out to determine the relative efficacy of the metallocene catalyst compositions of the present invention with rac- and meso-silyl bridged bis(indenyl)zirconium dichlorides having no substituents on the indenyl rings. In each instance, 1-hexene was used as the comonomer. Fluorided silica-alumina was used as the support-activator. The results are presented in Table 9.

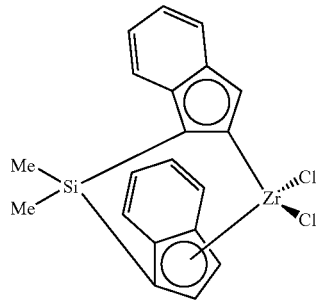

meso-Me$_2$SiInd$_2$ZrCl$_2$

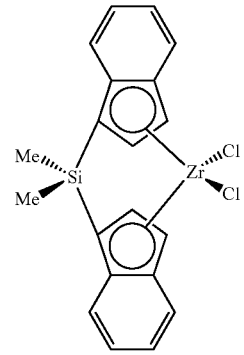

rac-Me$_2$SiInd$_2$ZrCl$_2$

The results indicate that both racemic and meso silyl bridged bis(indenyl)zirconium dichlorides having no substituents on the indenyl rings provide low melt index polyethylenes.

EXAMPLE 17

General Comparison with meso-ethylene (bis-Ind)ZrCl$_2$ and rac-ethylene (bis-Ind)ZrCl$_2$ Comparative polymerization runs (46–50) were carried out to determine the relative efficacy of the metallocene catalyst compositions of the present invention with racemic and meso ethylene bridged bisindenyl zirconium dichlorides having no substituents on the indenyl rings. The results are presented in Table 10.

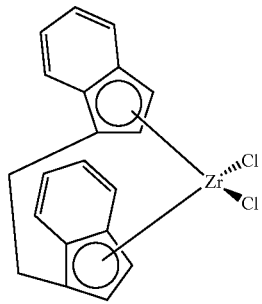

meso-EBIZrCl$_2$

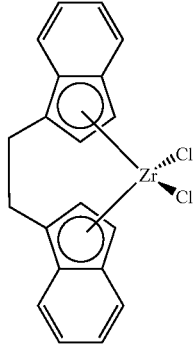

rac-EBIZrCl$_2$

TABLE 9

| | | Polymerization Conditions | | | | | | Results | |
| | | | | | | Support- | | | |
| Run | Metallocene | Time (min) | Temperature (C.) | Pressure (psi) | 1-Hexene Weight (g) | Activator Weight (mg) | TEA (15 wt %) (mL) | Metallocene Weight (g) | Solid PE (g) | MI |
|---|---|---|---|---|---|---|---|---|---|---|
| 44 | rac/meso (1/4) | 30 | 80 | 450 | 25.0 | 200 | 1.0 | 0.0015 | 141.0 | 0.0 |
| 45 | racemic | 30 | 80 | 450 | 25.0 | 200 | 1.0 | 0.0015 | 178.0 | 0.0 |

TABLE 10

| | | Polymerization Conditions | | | | | | | Results | |
|---|---|---|---|---|---|---|---|---|---|---|
| | | | | | | Support- | | | | |
| Run | Metallocene | Time (min) | Temperature (C.) | Pressure (psi) | 1-Hexene Weight (g) | Activator Weight (mg) | TEA (15 wt %) (mL) | Metallocene Weight (g) | Solid PE (g) | MI |
| 46 | meso | 30 | 80 | 450 | 25.0 | 200 | 1.0 | 0.0005 | 88.0 | 1.0 |
| 47 | meso | 30 | 80 | 450 | 40.0 | 200 | 1.0 | 0.0010 | 116.0 | 2.2 |
| 48 | rac/meso (1/1) | 30 | 80 | 450 | 25.0 | 200 | 1.0 | 0.0010 | 167.0 | 0.1 |
| 49 | racemic | 30 | 80 | 450 | 25.0 | 200 | 1.0 | 0.0005 | 237.0 | 0.0 |
| 50 | racemic | 30 | 80 | 450 | 40.0 | 200 | 1.0 | 0.0010 | 259.0 | 0.0 |

The results indicate that rac-ethylene bridged bisindenyl zirconium dichloride having no substituents on the indenyl rings provide low melt index polyethylene. Further, meso-ethylene bridged bisindenyl zirconium dichloride does not provide a melt index as high as the catalyst compositions of the present invention.

In sum, the metallocene compounds and catalyst compositions of the present invention provide significant improvements over presently available systems. Advantageously, the catalyst compositions produce polyethylenes that have a low molecular weight and high melt index, even when used in the absence of hydrogen. Additionally, the catalyst compositions provide high activities. Olefin polymerizations of the present invention proceed in the absence of costly aluminoxanes and organoborates.

The foregoing description has been presented for purposes of illustration and description. It is not intended to be exhaustive or to limit the invention to the precise examples or embodiments disclosed. Obvious modifications or variations are possible in light of the above teachings. The embodiment or embodiments discussed were chosen and described to provide the best illustration of the principles of the invention and its practical application to enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

What is claimed is:

1. A catalyst composition comprising an ansa-metallocene compound, an organoaluminum compound, and an activator-support, wherein:
   (a) the ansa-metallocene compound has the structure:
      (i)

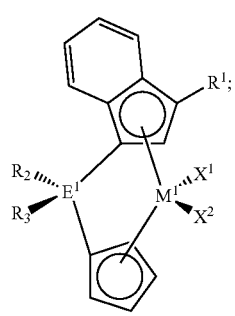

(A)

wherein $M^1$ is titanium or zirconium;

wherein $X^1$ and $X^2$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms;

wherein $R^1$ is an alkyl group having from 1 to about 20 carbon atoms, an alkyl silyl group, an alkenyl group, an alkynyl group, or a silyl group;

wherein $E^1$ is carbon or silicon;

wherein $R^2$ and $R^3$ independently are an alkyl group having from 1 to about 20 carbon atoms, an alkyl silyl group having from 1 to about 20 carbon atoms, an aryl group, an alkenyl group having from 2 to about 20 carbon atoms, an alkynyl group having from 2 to about 20 carbon atoms, a silyl group, or a hydride group; or (ii)

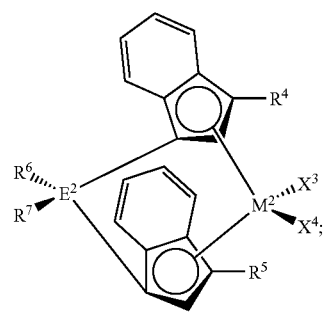

(B)

wherein $M^2$ is titanium or zirconium;

wherein $X^3$ and $X^4$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms;

wherein $R^4$ and $R^5$ independently are an alkyl group having from 1 to about 20 carbon atoms, an alkyl silyl group having from 1 to about 20 carbon atoms, an alkenyl group having from 2 to about 20 carbon atoms, or an alkynyl group having from 2 to about 20 carbon atoms;

wherein $E^2$ is carbon or silicon;

wherein $R^6$ and $R^7$ independently are an aryl group, an alkyl group having from 1 to about 20 carbon atoms, an alkenyl group having from 2 to about 20 carbon atoms, or an alkynyl group having from 2 to about 20 carbon atoms;

(b) the organoaluminum compound is a compound with the formula:

$Al(X^5)_n(X^6)_{3-n}$;

wherein $(X^5)$ is a hydrocarbyl having from 1 to about 20 carbon atoms;

$(X^6)$ is an alkoxide or an aryloxide having from 1 to about 20 carbon atoms, halide, or hydride; and n is a number from 1 to 3, inclusive; and (c) the activator-support comprises a chemically-treated solid oxide.

2. The catalyst composition of claim 1, wherein $R^1$ is a propyl group, a 1-butenyl group, or a trimethyl silyl group.

3. The catalyst composition of claim 1, wherein $R^2$ and $R^3$ independently are a methyl group.

4. The catalyst composition of claim 1, wherein $R^4$ and $R^5$ independently are a propyl group or an iso-butyl group.

5. The catalyst composition of claim 1, wherein $R^6$ and $R^7$ independently are a phenyl group or a methyl group.

6. The catalyst composition of claim 1, wherein the organoaluminum compound is trimethylaluminum, triethylaluminum, tri-n-propylaluminum, diethylaluminum ethoxide, tri-n-butylaluminum, diisobutylaluminum hydride, triisobutylaluminum, diethylaluminum chloride, or any combination thereof.

7. The catalyst composition of claim 1, wherein the chemically-treated solid oxide is fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, or any combination thereof.

8. The catalyst composition of claim 1, wherein the ansa-metallocene compound comprises $Me_2CCp(3-PrInd)ZrCl_2$, $Me_2CCp(3-ButenylInd)ZrCl_2$, $Me_2CCp(3Me_3SiInd)ZrCl_2$, meso-$Ph_2Si(3-PrInd)_2ZrCl_2$, meso-$Me_2Si(3-PrInd)_2ZrCl_2$, or meso-$Ph_2Si(3-i-BuylInd)_2ZrCl_2$.

9. The catalyst composition of claim 1, further comprising a cocatalyst selected from at least one aluminoxane, at least one organozinc compound, at least one organoboron compound, at least one ionizing ionic compound, or any combination thereof.

10. A process for producing a catalyst composition comprising contacting an ansa-metallocene compound, a chemically-treated solid oxide, and an organoaluminum compound, wherein:

(a) the ansa-metallocene compound has the structure:

(i)

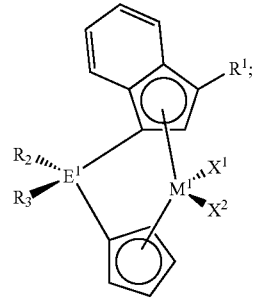

(A)

wherein $M^1$ is titanium or zirconium;

wherein $X^1$ and $X^2$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms;

wherein $R^1$ is an alkyl group having from 1 to about 20 carbon atoms, an alkyl silyl group, an alkenyl group, an alkynyl group, or a silyl group;

wherein $E^1$ is carbon or silicon;

wherein $R^2$ and $R^3$ independently are an alkyl group having from 1 to about 20 carbon atoms, an alkyl silyl group having from 1 to about 20 carbon atoms, an aryl group, an alkenyl group having from 2 to about 20 carbon atoms, an alkynyl group having from 2 to about 20 carbon atoms, a silyl group, or a hydride group; or (ii)

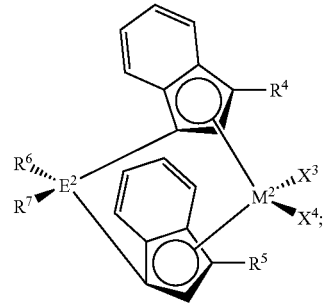

(B)

wherein $M^2$ is titanium or zirconium;

wherein $X^3$ and $X^4$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms;

wherein $R^4$ and $R^5$ independently are an alkyl group having from 1 to about 20 carbon atoms, an alkyl silyl group having from 1 to about 20 carbon atoms, an alkenyl group having from 2 to about 20 carbon atoms, or an alkynyl group having from 2 to about 20 carbon atoms;

wherein $E^2$ is carbon or silicon;

wherein $R^6$ and $R^7$ independently are an aryl group, an alkyl group having from 1 to about 20 carbon atoms, an alkenyl group having from 2 to about 20 carbon atoms, or an alkynyl group having from 2 to about 20 carbon atoms; and (b) the organoaluminum compound is a compound with the formula:

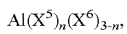

wherein ($X^5$) is a hydrocarbyl having from 1 to about 20 carbon atoms;

($X^6$) is an alkoxide or an aryloxide having from 1 to about 20 carbon atoms, halide, or hydride; and n is a number from 1 to 3, inclusive.

11. The process of claim 10, wherein the ansa-metallocene compound, chemically-treated solid oxide, and organoaluminum compound are contacted in any order.

12. The process of claim 10, further comprising precontacting the ansa-metallocene compound and the organoaluminum compound with an olefinic monomer for a first period of time to form a precontacted mixture.

13. The process of claim 12, wherein the first period of time is from about 0.1 hour to about 24 hours.

14. The process of claim 12, wherein the first period of time is from about 0.1 hour to about 1 hour.

15. The process of claim 12, further comprising contacting the precontacted mixture with the activator-support for a second period of time to form a postcontacted mixture.

16. The process of claim 15, wherein the second period of time is from about 0.1 hour to about 24 hours.

17. The process of claim 15, wherein the second period of time is from about 0.1 hour to about 1 hour.

18. The process of claim 15, wherein the postcontacted mixture is heated at a temperature of from about 0° F. to about 150° F.

19. A process for forming a polymer having a high melt index in the absence of hydrogen, the process comprising contacting a catalyst composition with at least one type of olefin monomer under polymerization conditions, the catalyst composition comprising an ansa-metallocene compound, a chemically-treated solid oxide, and an organoaluminum compound, wherein:

(a) the ansa-metallocene compound has the structure:

(i)

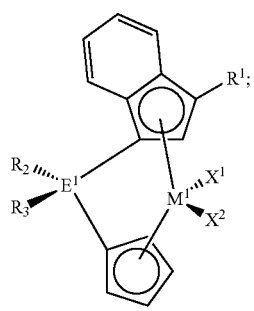

wherein $M^1$ is titanium or zirconium;

wherein $X^1$ and $X^2$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms;

wherein $R^1$ is an alkyl group having from 1 to about 20 carbon atoms, an alkyl silyl group, an alkenyl group, an alkynyl group, or a silyl group;

wherein $E^1$ is carbon or silicon;

wherein $R^2$ and $R^3$ independently are an alkyl group having from 1 to about 20 carbon atoms, an alkyl silyl group having from 1 to about 20 carbon atoms, an aryl group, an alkenyl group having from 2 to about 20 carbon atoms, an alkynyl group having from 2 to about 20 carbon atoms, a silyl group, or a hydride group; or (ii)

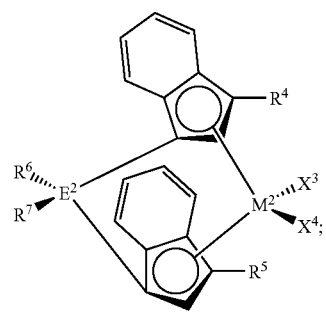

wherein $M^2$ is titanium or zirconium;

wherein $X^3$ and $X^4$ independently are a halogen, an alkyl group, an alkyl silyl group, an aryl group, an alkenyl group, an alkynyl group, H, OAr, $NR_2$, $NAr_2$, $BH_4$, $SO_3Ar$, $SO_3CH_3$, $SO_3CF_3$, or OR, wherein R is an alkyl group having from 1 to about 10 carbon atoms;

wherein $R^4$ and $R^5$ independently are an alkyl group having from 1 to about 20 carbon atoms, an alkyl silyl group having from 1 to about 20 carbon atoms, an alkenyl group having from 2 to about 20 carbon atoms, or an alkynyl group having from 2 to about 20 carbon atoms;

wherein $E^2$ is carbon or silicon;

wherein $R^6$ and $R^7$ independently are an aryl group, an alkyl group having from 1 to about 20 carbon atoms, an alkenyl group having from 2 to about 20 carbon atoms, or an alkynyl group having from 2 to about 20 carbon atoms;

(b) the organoaluminum compound is a compound with the formula:

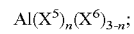

wherein ($X^5$) is a hydrocarbyl having from 1 to about 20 carbon atoms;

($X^6$) is an alkoxide or an aryloxide having from 1 to about 20 carbon atoms, halide, or hydride; and n is a number from 1 to 3, inclusive.

20. The process of claim 19, wherein the olefin monomer is ethylene.

21. The process of claim 19, further comprising contacting the catalyst composition with at least one comonomer.

22. The process of claim 21, wherein the comonomer is 1-butene, 1-pentene, 1-hexene, 1-octene, 1-decene, or styrene.

23. The process of claim 21, wherein the amount of comonomer is from about 0.01 to about 50 weight percent of the total weight of the monomer and comonomer.

24. The process of claim 19, wherein the polymerization conditions comprise a polymerization temperature of from about 60° C. to about 280° C.

25. The process of claim 19, wherein the molar ratio of the total moles of the metallocene compound to the organoaluminum compound is from about 1:1 to about 1:100.

26. The process of claim 19, wherein the catalyst composition and the at least one olefin monomer are contacted in a gas phase reactor, a loop reactor, or a stirred tank reactor.

27. A metallocene compound represented by the structure:

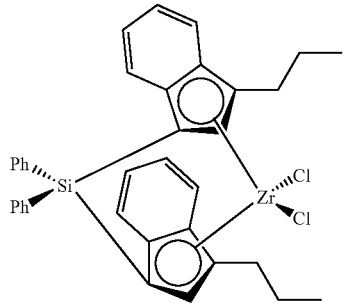

28. A metallocene compound represented by the structure:

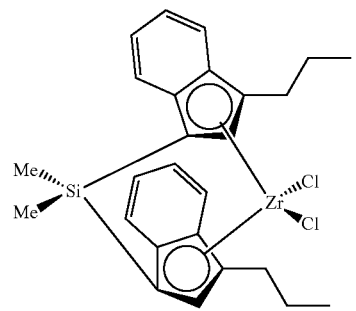

29. A metallocene compound represented by the structure:

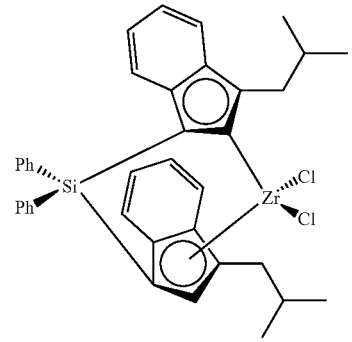

* * * * *